US012597520B2

(12) United States Patent
Mahajan et al.

(10) Patent No.: US 12,597,520 B2
(45) Date of Patent: Apr. 7, 2026

(54) SYSTEM AND METHOD FOR AUTOMATED DIAGNOSIS

(71) Applicants:EMPOWR-ME LLC, Troy, MI (US);
REGENTS OF THE UNIVERSITY OF MICHIGAN, Ann Arbor, MI (US)

(72) Inventors: Prashant Mahajan, Troy, MI (US);
Dilip Dubey, Troy, MI (US)

(73) Assignees: REGENTS OF THE UNIVERSITY OF MICHIGAN, Ann Arbor, MI (US);
EMPOWR-ME LLC, Troy, MI (US)

( * ) Notice: Subject to any disclaimer, the term of this patent is extended or adjusted under 35 U.S.C. 154(b) by 146 days.

(21) Appl. No.: 17/928,043

(22) PCT Filed: May 26, 2021

(86) PCT No.: PCT/US2021/034284
§ 371 (c)(1),
(2) Date: Nov. 28, 2022

(87) PCT Pub. No.: WO2021/242880
PCT Pub. Date: Dec. 2, 2021

(65) Prior Publication Data
US 2023/0215566 A1 Jul. 6, 2023

Related U.S. Application Data

(60) Provisional application No. 63/029,994, filed on May 26, 2020.

(51) Int. Cl.
*G16H 50/20* (2018.01)
*G16H 10/60* (2018.01)
*G16H 50/30* (2018.01)
(52) U.S. Cl.
CPC ............. *G16H 50/20* (2018.01); *G16H 50/30* (2018.01); *G16H 10/60* (2018.01)

(58) Field of Classification Search
CPC ........ G16H 50/20; G16H 50/30; G16H 10/60; G16H 40/67
See application file for complete search history.

(56) References Cited

U.S. PATENT DOCUMENTS 7,379,885 B1 * 5/2008 Zakim .................... G16H 20/10
600/300
11,189,376 B1 * 11/2021 Dudzinski .............. G16H 40/20
(Continued)

FOREIGN PATENT DOCUMENTS

WO 2019/075410 A1 4/2019

OTHER PUBLICATIONS

International Search Report and Written Opinion, Application No. PCT/US2021/034284, dated Oct. 26, 2021.
(Continued)

*Primary Examiner* — Mamon Obeid
*Assistant Examiner* — Malak M Nasser
(74) *Attorney, Agent, or Firm* — The Dobrusin Law Firm, P.C.; Daniela M. Thompson-Walters

(57) ABSTRACT

An automated diagnosis method executed by one or more computing devices including: a) receiving one or more data inputs inputted by a user into a user computing device; b) converting data from the one or more data inputs into stored data by one or more processors and storing within one or more storage mediums; c) determining one or more severity indexes based on the stored data with the one or more processors; d) predicting a presence of one or more medical conditions based on the one or more severity indexes by the one or more processors; and e) identifying a presence, an absence, or both of the one or more medical conditions by the one or more processors and transmitting for output to the user computing device.

20 Claims, 11 Drawing Sheets

(56) References Cited

U.S. PATENT DOCUMENTS

| | | | |
|---|---|---|---|
| 12,020,814 B1 * | 6/2024 | McNair .................. | G16H 50/70 |
| 2004/0122790 A1 | 6/2004 | Walker et al. | |
| 2006/0047188 A1 * | 3/2006 | Bohan .................... | A61B 5/411 |
| | | | 600/300 |
| 2008/0052120 A1 | 2/2008 | Iliff | |
| 2015/0339442 A1 | 11/2015 | Oleynik | |
| 2016/0259902 A1 | 9/2016 | Feldman et al. | |
| 2017/0323064 A1 | 11/2017 | Bates | |
| 2019/0080247 A1 | 3/2019 | Dubey et al. | |
| 2019/0209022 A1 | 7/2019 | Sobol et al. | |
| 2019/0216422 A1 | 7/2019 | Hamilton et al. | |
| 2020/0098476 A1 | 3/2020 | Loscutoff et al. | |
| 2020/0350056 A1 * | 11/2020 | Handal .................... | G09B 7/06 |
| 2022/0415491 A1 * | 12/2022 | Mansi .................. | G06T 11/001 |

OTHER PUBLICATIONS

India First Examination Report dated Nov. 11, 2025 (Application No. 202217074411.

* cited by examiner 22, 40

42

44

22, 40

46

48

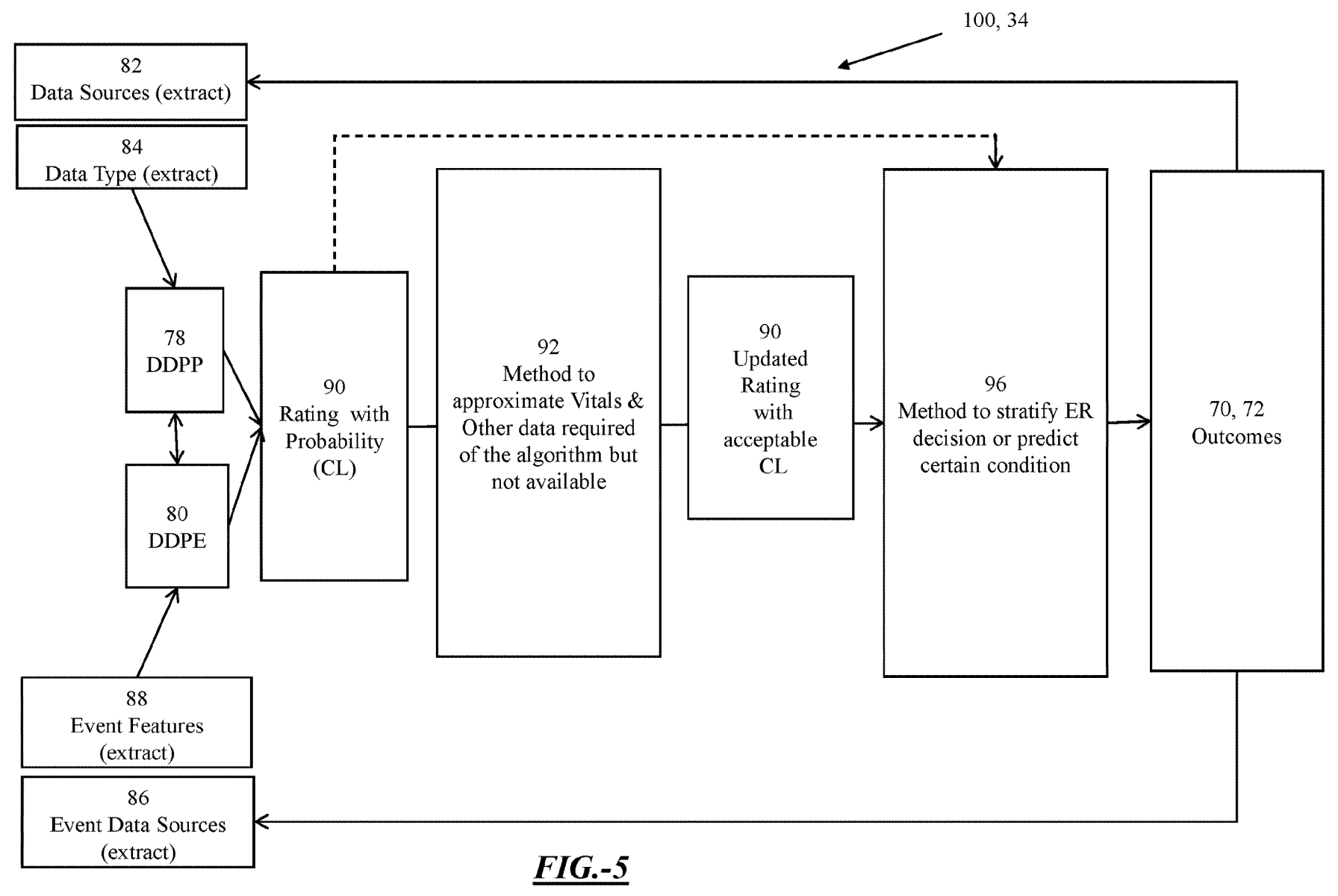

100, 34

82
Data Sources (extract)

84
Data Type (extract)

78
DDPP

80
DDPE

88
Event Features (extract)

86
Event Data Sources (extract)

90
Rating with Probability (CL)

92
Method to approximate Vitals & Other data required of the algorithm but not available 90
Updated Rating with acceptable CL 96
Method to stratify ER decision or predict certain condition 70, 72
Outcomes

*FIG.-5*

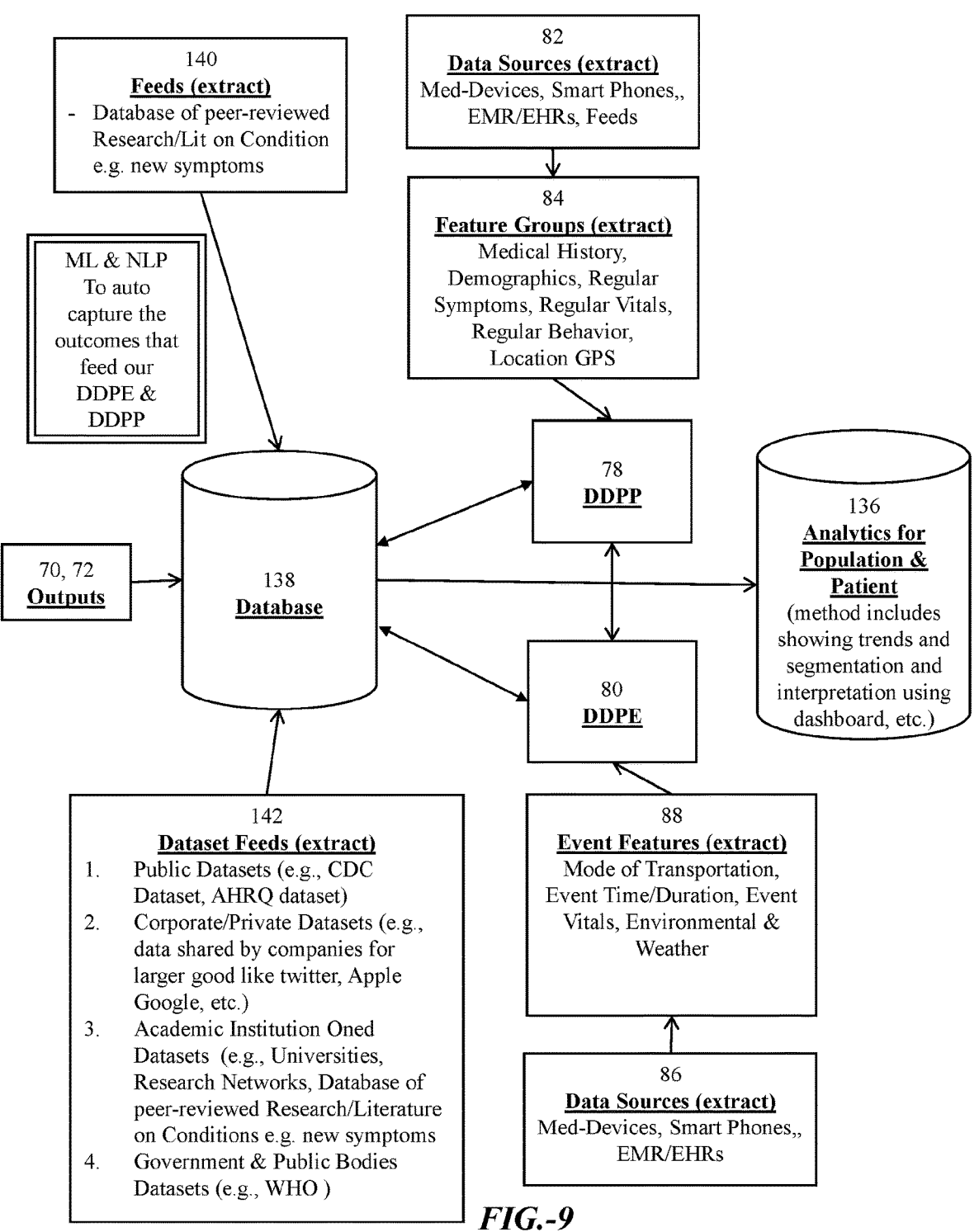

140
Feeds (extract)
- Database of peer-reviewed Research/Lit on Condition e.g. new symptoms ML & NLP
To auto capture the outcomes that feed our DDPE & DDPP

82
Data Sources (extract)
Med-Devices, Smart Phones,, EMR/EHRs, Feeds

84
Feature Groups (extract)
Medical History, Demographics, Regular Symptoms, Regular Vitals, Regular Behavior, Location GPS

78
DDPP

136
Analytics for Population & Patient
(method includes showing trends and segmentation and interpretation using dashboard, etc.)

70, 72
Outputs

138
Database

80
DDPE

142
Dataset Feeds (extract)
1. Public Datasets (e.g., CDC Dataset, AHRQ dataset)
2. Corporate/Private Datasets (e.g., data shared by companies for larger good like twitter, Apple Google, etc.)
3. Academic Institution Oned Datasets (e.g., Universities, Research Networks, Database of peer-reviewed Research/Literature on Conditions e.g. new symptoms
4. Government & Public Bodies Datasets (e.g., WHO )

88
Event Features (extract)
Mode of Transportation, Event Time/Duration, Event Vitals, Environmental & Weather

86
Data Sources (extract)
Med-Devices, Smart Phones,, EMR/EHRs

*FIG.-9*

SYSTEM AND METHOD FOR AUTOMATED DIAGNOSIS

CROSS REFERENCE TO RELATED APPLICATIONS

This PCT application claims priority benefit to U.S. Provisional Application No. 63/029,994, filed on May 26, 2020, the contents of which are incorporated herein by reference in their entirety.

FIELD

The present teachings relate to a system and method which may provide a medical diagnosis without first seeking medical care from a medical practitioner. The system and method may be particularly useful in automatically identifying the presence of one or more medical conditions, a severity of the one or more conditions, or both. The system and method may also be particularly useful in automatically providing one or more recommendations with respect to medical care and attention.

BACKGROUND

Individuals may have a tendency to avoid urgent medical care or regular medical care when symptoms are similar or overlap with influenza, a stomach virus, an average cold, a headache, stress, and the like. Symptoms may include fever, chills, sweating, cough, difficulty in breathing, sore throat, body aches, headaches, vomiting, diarrhea, fatigue, and the like. Individuals may avoid urgent care as they do not believe the symptoms are serious enough to pose a risk, do not have a family practitioner, are concerned with the cost of care, do not want to be exposed to the medical environment, or even have a general fear of medical environments. But there are times when these common symptoms can indicate the presence of a more serious illness or disease. For example, many of these symptoms may be an indication of COVID-19, heart attack, stroke, blood clotting, or the like. What is needed is a method for prompting individuals when to seek medical care and when they may be able to self-care at home.

After exposure to a virus, bacteria, or other pathogen, some diseases can be slower to present with their traditional "fingerprint" of symptoms (e.g., an incubation period). Some diseases may even only present very mild or no noticeable symptoms. In these cases, the individual may be considered asymptomatic or pre-symptomatic while being a carrier of the pathogen. For example, studies have found that possibly 25% to 50% of individuals with COVID-19 may be unaware they are carrying the SARS-CoV-2 virus. Studies have also found that individuals may be more contagious in the first few days after infection, while an individual is asymptomatic, and at the initial onset of symptoms. For example, with COVID-19, studies have found that individuals may be most contagious 48 to 72 hours before starting to experience symptoms and the first few days of being symptomatic. With influenza, studies have found that individuals may be contiguous up to 1 day before symptoms develop and up to 5 to 7 days after becoming sick. Even if an individual is asymptomatic toward what they physically feel, their body may signal the onset of an infection. Physical signs such as an elevated heart rate, breathing rate, and the like may provide a queue that the individual's body is working at fighting an infection. What is needed is a method to track health trends of an individual. What is needed is a method to identify variations from health trends of an individual to signal the onset of an infection before the onset of symptoms. What is needed is a method to alert a user they may be contagious such that they avoid exposing others.

Viruses in humans are generally detected via in-person detection methods. These methods may include culture methods (e.g., viral cultures) and nonculture methods (e.g., rapid diagnostic testing such as polymerase chain reaction devices). These tests can be quite accurate, but can be time-consuming, invasive, uncomfortable, and require the individual to be physically present. Additionally, the individual needs to know to seek medical attention to receive such a diagnostic test. Thus, what is needed is a method to identify the likelihood of a disease or illness requiring diagnostic testing under medical care and prompting an individual to seek medical care.

Another challenge in the medical field is the overuse of urgent care and emergency departments for non-serious illnesses or diseases. Individuals may use urgent care or emergency services as they may not have a primary care physician, are unsure of the severity of their symptoms, believe they may be attended to faster, or they are unable to obtain an appointment with their primary care physician. The overuse of urgent care and emergency facilities for non-urgent conditions results in the medical system being overutilized and unable to properly care for all patients in a timely manner. Medical practitioners in urgent care and emergency facilities may not be trained in diagnosing diseases and illnesses, may have to prioritize patients with visibly more urgent concerns (e.g., stroke, heart attack, excessive bleeding), and may not have access to a patient's medical history. Further, due to the difference in training of emergency practitioners and access to patient information, there is the possibility of misdiagnosing patients and even causing irreparable harm. Of the approximate 144 million individuals who visit emergency departments each year, about 7.5 million are misdiagnosed with about 3.5 million experiencing some level of harm from the misdiagnosis. These errors result in about $750 billion in annual costs with about 50% of harm being preventable. What is needed is a method if keeping non-urgent conditions outside of emergency and urgent care facilities so that medical practitioners can better focus on urgent conditions. What is needed is a method of keeping contagious individuals outside of urgent care and emergency service areas. What is needed is a method of routing individuals to the optimal location and/or type of practitioner for care if they are contagious.

SUMMARY

The present teachings relate to an automated diagnosis method comprising: a) receiving one or more data inputs; b) converting data from the one or more data inputs to stored data; c) determining one or more severity indexes based on the stored data; d) predicting a presence of one or more medical conditions based on the one or more severity indexes; and e) identifying and outputting a presence and/or absence of the one or more medical conditions.

The present teachings further relate to a vital approximation method comprising: a) receiving one or more data inputs from a user related to one or more vitals and which are only descriptions and/or estimates; b) retrieving one or more trends associated with the one or more vitals of the user and/or general population; c) calculating a vital value approximation; d) determining an impact of the value on a diagnosis method; and e) providing and/or retaining the vital value approximation from the diagnosis method.

The present teachings further relate to a system capable of performing the automated diagnosis method, the vital approximation method, or both.

The system and methods according to the teachings herein may provide an automated diagnosis method which is able to communication one or more medical care recommendation to a user, including whether or not to stay home, seek urgent care, or visit their normal medical practitioner within a reasonable time. The automated diagnosis method may be useful in diagnosing one or more medical conditions without the user (e.g., patient) having to seek medical care. The automated diagnosis process may be able to distinguish between urgent (e.g., severe) conditions and nonurgent (e.g., not severe) conditions. By distinguishing severity of the conditions, the automated diagnosis process may be useful in informing a user if they should go to urgent and/or emergency care facilities or they their condition is suitable for care at home or by the user's regular medical practitioner.

BRIEF DESCRIPTION OF DRAWINGS

FIG. 5 illustrates a method of using the system according to the teachings herein.

FIG. 9 illustrates a database of the system according to the teachings herein.

DETAILED DESCRIPTION

Figure 1:
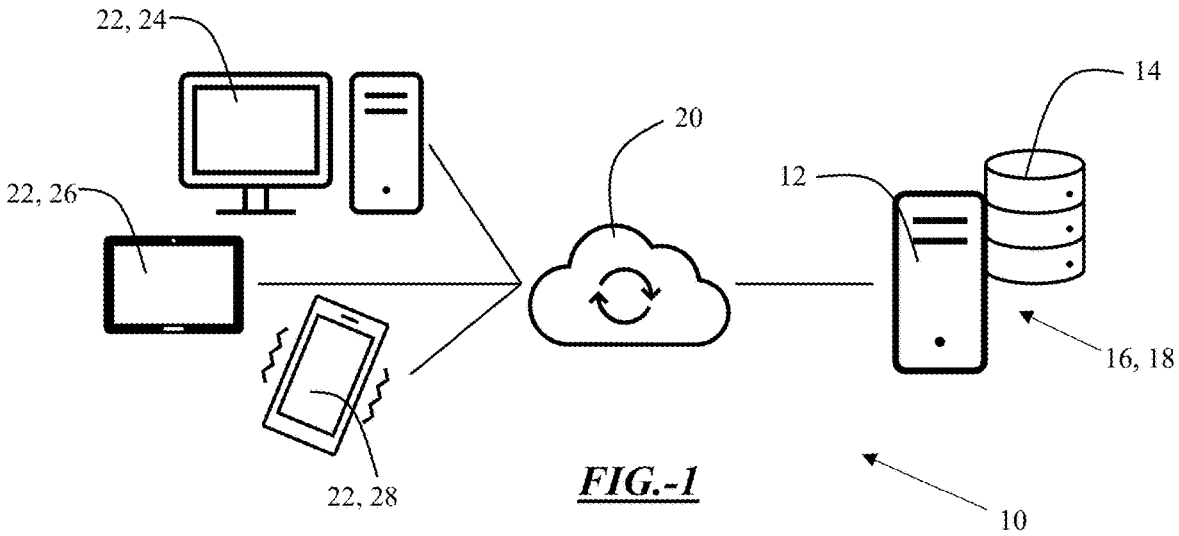
FIG. 1 illustrates a network diagram of a system according to the teachings herein.

The explanations and illustrations presented herein are intended to acquaint others skilled in the art with the present teachings, its principles, and its practical application. The specific embodiments of the present teachings as set forth are not intended as being exhaustive or limiting of the present teachings. The scope of the present teachings should be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The system and methods of the present disclosure may be used by one or more users (e.g., patients), medical practitioners (e.g., doctors, nurses, etc.), medical administrators (e.g., process engineers, analytics, etc.), the like, or any combination thereof. The system and methods of the present disclosure provide for a unique and unconventional means of diagnosing individuals with one or more conditions without seeing a medical practitioner, either in-person or virtually (e.g., telehealth); providing one or more medical care recommendations; suggesting one or more appropriate medical care facilities; estimating vitals without the use of one or more sensing devices; the like, or any combination thereof. For example, the system and method may inform an individual that he may be positive for COVID-19 with low severity and recommend visiting a local practitioner in the next few days. For example, the system and method may inform an individual that he may be positive for COVID-19 with high severity and recommend visiting urgent care and/or emergency services as soon as possible. The system and method may also identify the onset of one or more conditions overtime. The system and method may track the health of a user over a period of time and identify trends in the health of that user. The system and method may notice one or more irregularities, identify one or more conditions matching the irregularities, and/or inform a user of the presence of one or more conditions.

System

The present teachings may relate to a system for detecting one or more medical conditions, analyzing severity of one or more medical conditions, providing medical care recommendations to an individual, or any combination thereof. The system may allow for one or more computing devices (e.g., a user's mobile device or computer) to interact with an application. The application may receive one or more user inputs from the user related to the health of the user. The one or more user inputs may include one or more vitals. The application may include and/or cooperate with one or more algorithms, processes, and/or methods to identify one or more conditions and inform the user of the one or more conditions. The system may include one or more applications, user interfaces, sensing devices, computing devices, processors, servers, storage device mediums, databases, algorithms, processes, methods, the like, or a combination thereof.

The system may include one or more applications. The application (i.e., "computer program") may function to execute the method of the present disclosure. The application may be stored on one or more memory storage devices. The application may comprise one or more computer-executable instructions, algorithms, rules, processes, methods, user interfaces, menus, databases, the like, or any combination thereof. The computer-executable instructions, when executed by a computing device may cause the computing device to perform one or more methods described herein. The application may be downloaded, accessible without downloading, or both. The application may be downloadable onto one or more computing devices. The application may be downloadable from an application store (i.e., "app store"). An application store may include, but is not limited to, Apple App Store, Google Play, Amazon Appstore, the like, or any combination thereof. The application may be accessible without downloading onto one or more computing devices. The application may be accessible via one or more web browsers. The application may be accessible as a website. The application may interact and/or communicate through one or more interaction interfaces. The application may be utilized by one or more computing devices. The application may be utilized on one or more computing devices. The application may also be referred to as a dedicated application.

The dedicated application may work in conjunction with one or more other applications. Other applications may allow for data of a user, related to a user, or both to be collected by the application. One or more other applications may include one or more fitness and health applications, photograph applications, navigation applications, the like, or a combination thereof. Exemplary fitness and health applications may include Fitbit®, MyFitnessPal®, Runkeeper®, Health App by Apple®, Ava®, the like, or any combination thereof. Photograph applications may include a camera application, photo album application, the like, or a combination thereof. Navigation applications may include Google Maps®, Maps by Apple®, Waze®, the like, or a combination thereof. For example, the dedicated application may obtain a current heart rate, resting heart rate, weight, calories burned, temperature, breathing rate, sleep patterns, heart rate variability, photographs of an individual, nearest locations of medical facilities, the like, or any combination thereof. The one or more other applications may be on the same or a different computing device as the dedicated application. The dedicated application may be allowed access to the one or more other applications by a user, via user account information, via user login information, the like, or a combination thereof. The dedicated application may obtain data from the one or more other applications from the same computing device, via one or more networks, or both.

One or more computing devices may include one or more user interfaces. The one or more user interfaces may function to display information related to a user, receive user inputs related to a user, display data and/or one or more prompts to a user, or any combination thereof. The one or more user interfaces may function to receive a health status of an individual, display a health status of an individual, or both. The one or more user interfaces may be suitable for receiving data from a user. The one or more user interfaces may include one or more graphic user interfaces (GUI), audio interfaces, image interfaces, the like, or any combination thereof. One or more graphic user interfaces may function to display visual data to a user, receive one or more inputs from the user, or both. The one or more graphic user interfaces may include one or more screens. The one or more screens may be a screen located on a computing device. The one or more screens may be a screen on a mobile computing device, non-mobile computing device, or both. The one or more graphic user interfaces may include and/or be in communication with one or more user input devices, audio interfaces, image interfaces, the like, or any combination thereof. The one or more user input devices may allow for receiving one or more inputs from a user. The one or more input devices may include one or more buttons, wheels, keyboards, switches, mice, joysticks, touch pads (i.e., a touch-sensitive area, provided as a separate peripheral or integrated into a computing device, that does not display visual output), touch-sensitive monitor screens, microphones, the like, or any combination thereof. The one or more input devices may be integrated with a graphic user interface. An audio interface may function to project sound to a user and/or receive sound from a user. The audio interface may include audio circuitry, one or more speakers, one or more microphones, the like, or any combination thereof. An image interface may function to capture, receive, display, and/or transmit one or more images. An image interface may include one or more cameras. A user interface may function to display and/or navigate through one or more menus of the application.

A user interface may display one or more menus. The one or more menus may function to arrange related user inputs on a single user interface, prompt a user through inputting one or more instruction signals and/or data signals, guide the user in navigating the application, or any combination thereof. The one or more menus may include one or more account creation menus, log-in menus, medical history menus, vitals menus, wellbeing status menus, emergency conditions menus, daily symptoms menus, diagnosis menus, the like, or any combination thereof. Data entered by a user in one or more menus may be transmitted to one or more databases; may be converted from one or more data signals to data entries; may be processed in one or more methods, processes, and/or algorithms; or nay combination thereof. Data entered by a user may be transmitted into one or more dynamic digital profiles of the patient, of the event, or both. Data entered by a user may be associated with one or more records associated with the user, a user identification key, or both. One or more menus may be displayed on a single screen or may prompt the user through multiple, sequential screens; sub-screens (e.g., pop-ups); or both.

One or more account creation menus may allow a user to create an account with the system. One or more account creation menus may collect data associated with a name, username, email, password, gender, age, height, weight, zip code, race, ethnicity, education, income, profession, other demographic information, the like, or any combination thereof.

One or more log-in menus may collect log-in information to allow a user to log-in to their account, add data to their account, receive a medical diagnosis, the like, or a combination thereof. One or more log-in menus may collect data associated with a username, password, the like, or a combination thereof.

One or more medical history menus may allow for a user to input one or more medical conditions the user may currently be experiencing, may have had in the past, may be predisposed to (e.g., medical conditions of mother, father, grandparents, etc.), or any combination thereof. One or more medical conditions may include heart disease, high and/or low blood pressure, lung disease, diabetes, neurologic disease, kidney failure, liver failure, cancer, weakened immunity, autoimmune disease, pregnancy, obesity, the like, or any combination thereof. One or more medical conditions may also include one or more habits. One or more habits may include smoking, drinking, exercising, the like, or any combination thereof.

One or more vitals menus may allow for a user to input one or more vitals of the user at the time of entry. One or more vitals may include heart rate, body temperature, respiration rate, blood pressure, the like, or any combination thereof.

One or more wellbeing status menus may allow for a user to input their general health status. Health status may be ranked, such as 1 (bad, in extreme discomfort) to 10 (great, no health issues or symptoms). Health status may be shown as visual indicators, such as thumbs down to thumb up, smiley face to happy face, the like, or any combination thereof.

One or more emergency menus may allow for a user to input symptoms indicative of an emergency (e.g., critical symptoms). One or more critical symptoms may include breathing issues, blue colored lips and/or face, speech issues (e.g., slurred speech), extreme fatigue (e.g., inability to stay awake), chest pain (e.g., possibility indicative of stroke, heart attack), severe dizziness and/or lightheadedness, the like, or any combination thereof. One or more emergency menus may display an emergency prompt. An emergency prompt may function to alert a user to seek immediate emergency assistance.

One or more daily symptoms menus may allow for a user to input one or more symptoms they may be experiencing (e.g., current symptoms). One or more current symptoms may include fever, chills, sweating, difficulty breathing, sore throat, body aches, headache, vomiting, diarrhea, fatigue, runny nose, phlegm, rash, the like, or any combination thereof. One or more current symptoms may also include one or more photographs of a user showing one or more physical symptoms (e.g., rash, acne, burn, wound, etc.).

One or more diagnosis menus may function to communicate to a user a presence of a condition, a severity and/or risk of the condition, a medical care recommendation, one or more nearby medical facilities, one or more general status updates, the like, or any combination thereof. One or more general status updates may include a heat map of current cases of the same and/or a similar condition of which the user has been diagnosed, a heat map showing how many users are using the system and/or application, the like, or any combination thereof.

A user may be prompted to one or more of the menus when creating an account, each time the user logs into the system, after providing input into a menu, or any combination thereof. For example, a user may only be prompted through the one or more account creation menus, medical history menus, or both when creating an account. For example, a user may always be prompted through an emergency menu and daily symptom menus when logged in to the application.

The system may include, connect to, or be free of one or more sensing devices. The one or more sensing devices may function to detect one or more vital signals, physiological signals, the like, or any combination thereof. The one or more sensing devices may be wired, wireless, noncommunicative, or any combination thereof. Wired may mean that the one or more sensing devices are in direct electrical communication with an electronic processor, memory storage device, user interface, or a combination thereof via one or more wires such that signals received by the one or more sensing devices are transmitted via the one or more wires. Wireless may mean that the one or more sensing devices are not physically connected to the electronic processor, memory storage device, user interface, or a combination thereof and may transmit the signals received by one or more wireless modes of communication. The electronic processor, memory storage device, user interface, or combination thereof may be part of the user mobile device, another computing device, or combination thereof. Wireless modes may include Wi-Fi, Bluetooth®, NFC, and the like. Noncommunicative may mean that the sensing device is not in communication with any components of the system, a user may rely on an output of the sensing device, a user may enter the output of the sensing device into the application (e.g., using the user interface), or any combination thereof. One or more sensing devices may include any device capable of detecting and measuring one or more vital signals, physiological signals, or any combination thereof of a human or other animal. One or more sensing devices may be included, separate from, or both one or more user computing devices, medical facility computing devices, or both. One or more sensing devices may include one or more thermometers, heart rate monitors, pulse oximeter, other applications of a computing device, be embedded within the dedicated application, be included within one or more wearable accessories, the like, or any combination thereof. One or more heart rate monitors may include one or more optical heartbeat sensors. Optical heartbeat sensors may be integrated into wearable accessories (e.g., ring, watch), mobile devices (e.g., mobile phone, tablet), and the like.

The system may include one or more computing devices. The one or more computing devices may function to allow a user to interact with an application; execute one or more algorithms, methods, and/or processes; receive and/or transmit one or more signals, convert one or more signals to data entries, retrieve one or more data entries from one or more storage mediums, or any combination thereof. The one or more computing devices may include and/or be in communication with one or more processors, storage mediums, servers, networks, user interfaces, other computing devices, the like, or any combination thereof. The one or more or more computing devices may communicate via one or more interaction interfaces (e.g., an application programming interface ("API")). The computing device may be one or more personal computers (e.g., laptop or desktop), mobile devices (e.g., mobile phone, tablet, smart watch, etc.), or any combination thereof. The computer device may include one or more user computing devices, medical facility system computing devices, diagnostic computing systems, patient record computing systems, the like, or any combination thereof. One or more user computing devices may be associated with one or more users seeking a medical diagnosis, diagnosis risk, medical care recommendation, the like, or any combination thereof. Medical facility system computing device(s) may be associated with one or more medical facilities and used by one or more medical practitioners (e.g., doctor, nurse, administrative staff). Diagnostic computing systems may be associated with the databases and methods disclosed herein, may be in communication with one or more user computing devices, or other computing devices, or any combination thereof. One or more patient record computing systems may be computing systems associated with storing electronic medical records associated with one or more patients, may be located at a medical facility, may be remote from a medical facility, or any combination thereof.

The system may include one or more processors. The one or more processors may function to analyze one or more signals and/or data from one or more sensing devices, memory storage devices, databases, user interfaces, or any combination thereof; convert one or more signals to data suitable for analysis and/or saving within a database (e.g., data conversion, data cleaning); or a combination thereof. The one or more processors may be located in one or more sensing devices, user interfaces, computing devices, the like, or any combination thereof. The one or more processors may or may not be cloud-based (e.g., remote from other portions of the system). One or more processors may include a single or a plurality of processors. One or more processors may be in communication with one or more other processors. The one or more processors may function to process data, execute one or more algorithms to analyze data, or both. Processing data may include receiving, transforming, outputting, executing, the like, or any combination thereof. One or more processors may be part of one or more hardware, software, systems, or any combination thereof. One or more hardware processors may include one or more central processing units, multi-core processors, front-end processors, the like, or any combination thereof. The one or more processors may be non-transient. The one or more processors may be referred to as one or more electronic processors. The one or more processors may convert data signals to data entries to be saved within one or more storage mediums. A data signal may be a signal associated with an input from a user interface. A data entry may be an entry stored within one or more databases. The one or more processors may access one or more algorithms, processes, and/or methods to analyze one or more data entries and/or data signals. The one or more processors may access one or more algorithms saved within one or more memory storage mediums. The one or more processors may execute one or more methods for an individual and detecting the presence of a medical condition, a risk of a medical condition, a medical care recommendation, a diagnosis process, vital approximation, data conversion to comprehend and/or store data within one or more databases, one or more machine learning processes, the like, or any combination thereof. The one or more processors may execute the one or more methods, processes, and/or algorithms via one or more algorithms stored within and accessible from one or more memory storage devices; data stored within and accessible from one or more databases; or both.

The system may include one or more memory storage devices (e.g., electronic memory storage device). The one or more memory storage devices may store data, databases, algorithms, processes, methods, or any combination thereof. The one or more memory storage devices may include one or more hard drives (e.g., hard drive memory), chips (e.g., Random Access Memory "RAM)"), discs, flash drives, memory cards, the like, or any combination thereof. One or more discs may include one or more floppy diskettes, hard disk drives, optical data storage media including CD ROMs, DVDs, and the like. One or more chips may include ROMs, flash RAM, EPROMs, hardwired or preprogrammed chips, nanotechnology memory, or the like. The one or more memory storage devices may include one or more cloud-based storage devices. The data stored within one or more memory storage devices may be compressed, encrypted, or both. The data stored within one or more memory storage devices may comply with health privacy regulations (e.g., Health Insurance Portability and Accountability Act). The one or more memory storage devices may be located within one or more sensing devices, computing devices, one or more processors, one or more user interfaces, or any combination thereof. One or more memory storage devices may be referred to as one or more electronic memory storage devices. One or more memory storage devices may be non-transient. One or more memory storage mediums may store one or more data entries in a native format, foreign format, or both. One or more memory storage mediums may store data entries as objects, files, blocks, or a combination thereof. The one or more memory storage mediums may include one or more algorithms, methods, algorithms, rules, databases, data entries, the like, or any combination therefore stored therein. The one or more memory storage mediums may store data in the form of one or more databases.

One or more computing devices may include one or more databases. The one or more databases may function to receive, store, and/or allow for retrieval of one or more data entries. The data entries may be values associated with one or more detected signals; results from one or more algorithms, processes, rules, and/or methods; or any combination thereof. The one or more databases may be located within one or more memory storage devices. The one or more databases may include any type of database able to store digital information. The digital information may be stored within one or more databases in any suitable form using any suitable database management system (DBMS). Exemplary storage forms include relational databases (e.g., SQL database, row-oriented, column-oriented), non-relational databases (e.g., NoSQL database), correlation databases, ordered/unordered flat files, structured files, the like, or any combination thereof. The one or more databases may store one or more classifications of data models. The one or more classifications may include column (e.g., wide column), document, key-value (e.g., key-value cache, key-value store), object, graph, multi-model, or any combination thereof. One or more databases may be located within or be part of hardware, software, or both. One or more databases may be stored on a same or different hardware and/or software as one or more other databases. One or more databases may be located in a same or different non-transient storage medium as one or more other databases. The one or more databases may be accessible by one or more processors to retrieve data entries for analysis via one or more algorithms, methods, rules, processes, or any combination thereof. The one or more databases may include a single database or a plurality of databases. One database may be in communication with one or more other databases. One or more other databases may be part of or separate from the system. One or more databases separate from the system may include one or more public datasets (e.g., Centers for Disease Control and Prevention ("CDC"), Agency for Healthcare Research and Quality ("AHRQ")), corporate datasets and/or private datasets (e.g., data sets from larger companies provided for the greater good, such as Twitter®, Apple®, and Google®), academic datasets (e.g., data sets from universities, research networks, peer-reviewed research, literature on new and known conditions, etc.), government and/or public body data sets (e.g., World Health Organization ("WHO")), the like, or a combination thereof. One or more databases may include a global database. One or more databases may be connected to one or more other databases via one or more networks. For example, a database of the system may be in communication with one or more other databases via the Internet. The database may also receive one or more outputs of the system. The outputs may include diagnosis, medical care recommendation, or both. The database may be able to have the data outputted, sorted, filtered, analyzed, the like, or any combination thereof. For example, patient data within the database may be able to be analyzed to determine one or more trends, deviations, variability, conditions, the like, or any combination thereof. As another example, population data for the entire or a portion of the dataset within a database may be analyzed to determine one or more trends, deviations, variability, conditions, the like, or any combination thereof. The one or more databases may include one or more patient records, medical records, user accounts, condition locations, threshold indexes, tested models, model toolbox, digital profiles, the like, or any combination thereof. One or more digital profiles may include one or more dynamic digital profile of one or more patients (DDPP), one or more dynamic digital profiles of one or more events (DDPE), the like, or any combination thereof. The database may be suitable for storing a plurality of records.

One or more databases may include one or more records. The one or more records may function to store one or more data entries associated with one or more users. A record may include one or more data entries associated with one or more signals. The one or more signals may be collected via a user interface during a single visit or a plurality of visits to the application. The visit may be the user, a medical practitioner, or both. A user may be associated with a user identification key. One or more records in one or more databases may be filtered by a user identification key to execute one or more algorithms, processes, rules, or any combination thereof related to the user. For example, one or more digital profile databases may store records associated with multiple users over multiple visits. One or more algorithms, methods, and/or processes may filter the data for a specific user by a user identification key to provide for a diagnosis of that specific user. One or more records may include one or more data entries associated with identification data, log-in information, medical history, medical conditions, vitals, emergency conditions, wellbeing, critical symptoms, current symptoms, the like, or any combination thereof.

The system of the present disclosure may be integrated and/or include one or more networks. The computing devices may be in selective communication with one or more networks. The one or more networks may be formed by placing two or more computing devices in communication with one another. One or more networks may include one or more communication hubs, communication modules, computing devices, processors, databases, servers, memory storage devices, sensing devices, the like, or any combination thereof. One or more networks may be free of and/or include one or more communication hubs (e.g., router, wireless router). One or more computing devices of the system may be directly connected to one another without the use of a communication hub. One or more networks may be connected to one or more other networks. One or more networks may include one or more local area networks ("LAN"), wide area networks ("WAN"), virtual private network ("VPN"), intranet, Internet, cellular networks, the like, or any combination thereof. The network may be temporarily, semi-permanently, or permanently connected to one or more computing devices, or any combination thereof. A network may allow for one or more computing devices to be connected to the computing device to transmit one or more data signals to the one or more computing devices, receive one or more data signals from the one or more computing devices, or both. The network may allow for one or more computing devices to receive one or more data entries from and/or transmit one or more data entries to one or more storage media. The network may allow for transmission of one or more signals, status signals, data entries, instruction signals, or any combination thereof, for processing by one or more processors.

User Record Entry Process (Regular Diagnosis Process)

The teachings herein relate to a method of user entry for medical diagnosis of one or more conditions. A user may interact with an application via one or more computing devices, enter one or more inputs via one or more user interfaces, or both. The method may cooperate with the system of the present disclosure. A method of user entry for medical diagnosis may include one or more of the following steps: logging-in, providing vitals, providing an overall wellbeing status, providing critical symptoms, providing current symptoms, receiving a diagnosis, the like, or any combination thereof.

A method of user entry for medical diagnosis may include logging-in. Logging-in may allow for a user to add data pertaining to their health to one or more records associated to themselves, see data associated with data entries tied to their account, or both. Logging-in may start by opening the application. Opening the application may include opening an application, visiting a website, or both on a computing device. Logging-in may include a user interacting with a log-in menu. Logging-in may include the user submitting their username, password, or both. Logging-in may use other credentials such as facial recognition, fingerprint scanning, email address, or any other forms of logging into computing devices and applications. Upon successfully logging-in, a user may be prompted to enter current health data.

A method of user entry for medical diagnosis may include providing one or more vitals. One or more vitals may allow for a diagnosis method to determine a diagnosis of the individual. One or more vitals may allow for the application to determine one or more health trends of the individual. Providing one or more vitals may include interacting with one or more vitals menus, entering data associated with one or more vitals, connecting one or more sensing devices to the application, or any combination thereof. One or more vitals may include heart rate, respiration rate, temperature, blood pressure, the like, or a combination thereof. One or more vitals may be entered as one or more precise numbers, number estimates, descriptions by feel, the, or any combination thereof. Precise numbers may be those obtained from one or more sensing devices. Number estimates may be those obtained by one or more manual methods of obtaining one or more vitals. For example, obtaining a heart and/or pulse rate estimate may include physically feeling the pulse (e.g., fingers over inside of wrist or on neck) and counting the number of pulses over a period of time. As another example, obtaining a breathing rate estimate may include counting a number of breaths over a period of time. A description by feel may be one or more descriptions related to one or more vitals. A description by feel may be referred to as a vital approximation or a portion of a vital approximation. For example, a temperature above normal may be entered as feeling hot, sweating, chills, shaking, hot skin, flushed skin, the like, or any combination thereof etc. As another example, a rapid heart rate may be entered as rapid heartbeat, fluttering in chest, feeling pulse, short of breath, the like, or any combination thereof. As another example, an individual may use one or more sensing devices separate from the computing device with the application to determine one or more vitals. For example, a user may use a thermometer to obtain their temperature. As another example, a user may refer to a fitness watch to obtain their heart rate. An individual may enter in the one or more vitals into one or more vitals menus. An individual may allow for and/or initiate the application to communicate with one or more sensing devices, other applications, or both to obtain one or more vitals. The one or more sensing devices may communicate wireless or via a wired connection. The one or more sensing devices may communicate over a network, via the same mobile device, or both. An individual may use one or more vital approximation methods within the application to determine and enter one or more vitals.

A method of user entry for medical diagnosis may include providing an overall wellbeing status. An overall wellbeing status may allow for the diagnosis method to determine a severity of a potential condition. Providing one or more wellbeing statuses may include interacting with one or more wellbeing status menus, entering data associated with one or more wellbeing statuses, or both. A wellbeing status may be provided as a verbal language, a visual description, one or more written words, the like, or any combination thereof. Verbal language may be transmitted via one or more audio interfaces to the application. Visual descriptions and/or more written words may be transmitted via one or more graphic user interfaces. Verbal language may include words indicating the overall feeling, presence, or lack of pain, discomfort, mood, the like, or any combination thereof. One or more visual descriptions may include a facial emotion scale, a thumbs up/down scale, a numerical scale, the like, or any combination thereof. One or more written words may include words which can be typed and/or selected on the wellbeing status menu which indicate the wellbeing of the individual.

A method of user entry for medical diagnosis may include providing one or more critical symptoms. Inputting one or more critical symptoms allows for the application to direct an individual to seek urgent medical attention. Inputting one or more critical symptoms may allow for the application to alert a user for prompt medical attention as opposed to continuing within the application and user entry process. Providing one or more critical symptoms may include interacting with one or more emergency condition menus. One or more critical symptoms may include breathing issues, blue colored lips and/or face, speech issues (e.g., slurred speech), extreme fatigue (e.g., inability to stay awake), chest pain (e.g., possibility indicative of stroke, heart attack), severe dizziness and/or lightheadedness, the like, or any combination thereof. One or more critical symptoms may be selected from one or more buttons, drop downs, other visual inputs, or any combination thereof on a graphic user interface. One or more critical symptoms may be input via one or more audio interfaces by the user speaking into a computing device. If one or more critical symptoms are selected, the application may prompt a user to seek emergency assistance. The application may automatically or upon instruction from a user contact emergency assistance (e.g., call 911). The application may automatically or upon user instruction submit data related to the user to a medical facility, medical practitioner, or both.

A method of user entry for medical diagnosis may include providing one or more current symptoms. One or more current symptoms may allow for the application to determine if a user is experiencing one or more medical conditions, what type of medical care may be needed, or both. One or more current conditions may allow for the application to identify trends in a user's health specific to the individual. Providing one or more current symptoms may include interacting with one or more daily symptom menus. One or more daily symptoms may be those symptoms a user is currently experiencing (e.g., current symptoms). One or more current symptoms may include fever, chills, sweating, difficulty breathing, sore throat, body aches, headache, vomiting, diarrhea, fatigue, runny nose, phlegm, rash, chest pain, muscle aches, the like, or any combination thereof. One or more current symptoms may be inputted via one or more graphic user interfaces, audio interfaces, photography interfaces, the like, or any combination thereof. The individuals may select one or more current symptoms from one or more buttons, drop boxes, checkboxes, lists, anatomical images, the like, or any combination thereof. The individuals may vocally describe one or more current symptoms and submit using a microphone. The individuals may upload one or more photographs, videos, or both showing one or more current symptoms using a camera.

A method of user entry for medical diagnosis may include receiving a diagnosis. Receiving the medical diagnosis allows for the user to determine their condition, seek medical care, seek the appropriate kind of medical care (e.g., family practitioner, urgent care, emergency services), the like, or any combination thereof. Receiving of the medical diagnosis may involve the user interacting with one or more diagnosis menus. The one or more diagnosis menus may display information received from one or more diagnosis methods. The one or more diagnosis menus may display one or more diagnoses (e.g., medical condition(s)), severity, recommended medical care, the like, or any combination thereof.

User Account Creation Process

The teachings herein relate to a user account creation process using the system as taught herein. A user account creation process may allow for a user to repeatedly interact with an application, store data related to themselves in the application, proceed with a user record entry process, or any combination thereof. The user account creation process may be suitable for using with the system according to the present teachings. A user may interact with an application via one or more computing devices, enter one or more inputs via one or more user interfaces, or both. A user account creation process may include creating log-in information, providing personal information, providing demographic information, providing medical history information, the like, or any combination thereof. A user account creation process may include one or more steps of providing identification information, medical history, or both.

A user account creation process may include a user submitting one or more pieces of identification data. Identification data may allow for a user to subsequently log-in to the application, provide demographic information about the user, provide general health data about the user, provide medical predispositions of the user, the like, or any combination thereof. The user may interact with one or more account creation menus. Submitting identification data may include setting-up log-in information. Setting up log-in information may include providing a name, username, email, password, facial images, fingerprint scans, voice recordings, the like, or any combination thereof. Log-in information may allow for the user to subsequently log-into the application. Submitting identification data may include submitting one or more pieces of personal information about the user. One or more pieces of personal information may include a gender, age, height, weight, zip code, race, ethnicity, education, marriage status, number of children, income, profession, other demographic information, the like, or any combination thereof of the user.

A user account creation process may include a user submitting one or more pieces of medical history. Medical history may allow for the application to better tailor the diagnosis process to the user, may increase accuracy of a medical diagnosis, or both. A user may interact with one or more medical history menus to submit one or more pieces of medical history. A user may input one or more medical conditions the user may currently be experiencing, may have had in the past, may be predisposed to (e.g., medical conditions of mother, father, grandparents, etc.), the like, or any combination thereof. One or more medical conditions may include heart disease, high and/or low blood pressure, high cholesterol, lung disease, diabetes, neurologic disease, kidney failure, liver failure, cancer, weakened immunity, autoimmune disease, pregnancy, obesity, the like, or any combination thereof. One or more medical conditions may also include one or more habits. One or more habits may include smoking, drinking, exercising, the like, or any combination thereof.

An individual may access and/or edit their identification data, medical history, or both after user account creation. A user may access this information for editing via the application.

Medical Condition Detection

The system and method of the present teachings may be particularly useful in detecting one or more conditions (e.g., "medical condition"). One or more user inputs may function to identify one or more indicators. One or more indicators may identify the presence of a medical condition. A condition may include one or more viral infections, bacterial infections, disease, illness, medical events, and/or other conditions. One or more viral infections may include influenza, common colds, SARS-CoV, SARS-CoV-2 (COVID-19), MERS-CoV, the like, or any combination thereof. A medical disorder or condition may include glucose events, such as low and/or high blood glucose levels (e.g., hypoglycemia, hyperglycemia). One or more medical events may include substantially spontaneous events such as stroke, heart attack, aneurysm, the like, or any combination thereof. A condition may be identifiable by one or more indicators specifically indicating the presence of the condition. A condition may be identifiable by one or more deviations from one or more trends from user data associated with the user (e.g., "patient").

User inputs may be related to one or more vital signs, other physiological signs, or both. One or more vital signs may include a pulse rate, temperature, respiration rate, blood pressure, the like, or any combination thereof. The one or more vital signs may be indicative of an individual's essential body functions. One or more physiological signs may include fatigue, peripheral blood flow, peripheral capillary oxygen saturation, sweat rate, skin conductance, skin temperature, headache, coughing, one or more gastrointestinal issues, muscle weakness, the like, or any combination thereof. One or more physiological signs may include one or more conditions detected by one or more imaging methods. One or more imaging methods may include photography, ultrasonic imaging, x-ray imaging, magnetic resonance imaging, the like, or any combination thereof. One or more physiological signs may be stored within the user record by one or more medical practitioners, the user, or both. The one or more vital signs, physiological signs, or both may cooperate together to identify the presence of one or more conditions.

Diagnosis Method

The teachings of the present application relate to a diagnosis method using the system according to the teachings herein. The diagnosis method may use one or more user inputs related to a user account to determine the presence and/or absence of a medical condition, determine one or more health trends of a user, recommend medical care, determine the severity of one or more conditions, the like, or any combination thereof. The diagnosis method may be useful with the system of the present teachings, may be processed by the system of the present teachings, or both. The diagnosis method may include one or more of the following steps: receiving one or more data inputs; converting data from data inputs to stored data; determining a severity index; predicting a presence of one or more medical conditions; identifying and outputting the presence and/or absence of one or more medical conditions; the like; or any combination thereof.

A diagnosis method may include receiving one or more user data inputs. The one or more user data inputs may be input via a user record entry process, account creation process, or both. The one or more data inputs may be from a user, from one or more medical practitioners, one or more sensing devices, via a user interface, via the application, the like, or any combination thereof. One or more data inputs may include text, audio, numerical, and/or visual inputs. One or more data inputs may include one or more data signals, data entries, or both related to a patient, an event, or both. A patient may be considered the user having the user account. An event may be considered the singular instance of logging in, a diagnosis resulting in a medical condition, or both. The one or more data inputs may include identification data, log-in information, medical conditions, vitals, wellbeing status, critical symptoms, current symptoms, mode of transportation (e.g., before, during, or after), time (e.g., time of input), duration (e.g., duration of one or more current symptoms), environment, weather, the like, or any combination thereof. One or more user data inputs may be converted to stored data, directed toward one or more databases, or both. One or more data inputs may be directed to, stored in, or both a dynamic digital profile of the patient (DDPP), a dynamic digital profile of the event (DDPE), or both. One or more processors may direct the one or more data inputs for storage or other processing methods.

A diagnosis method may include converting data from data inputs into stored data. The data conversion method may function to convert one or more data inputs into stored data, convert unstructured data into structured data, store data in one or more digital profiles, or both. The data conversion method may be executed by one or more processors. The one or more processors may be of one of more user computing devices, diagnostic computing devices, the like, or a combination thereof. The data conversion method may be automatically executed upon one or more data inputs being input. The data conversion method may receive one or more data inputs. One or more data inputs may be structured, unstructured, or both. One or more structured data inputs may be directed to and/or stored in one or more dynamic digital profiles. One or more structured data inputs related to a user and/or entered by a user may be transmitted toward and stored in a dynamic digital profile of the patient (DDPP), of the event (DDPE), or both associated with the user.

One or more unstructured data inputs may go through a data extraction process. A data extraction process may be any suitable process for converting human language into language understood and/or useful by one or more computing devices. A data extraction process may include one or more natural language processing methods. One or more natural language processing methods may include sentence tokenization, word tokenization, text lemmatization, text stemming, stop words, regex, bag of words, term frequency-inverse document frequency (tf-idf), the like, or any combination thereof. The unstructured data may be considered structured after undergoing one or more data extraction processes.

The structured data may be directed toward one or more data cleaning processes. The one or more data cleaning processes may function to decode one or more user inputs received as an image, video, and/or voice; the like, or a combination thereof. The one or more data cleaning processes may include one or more types of machine learning. One or more types of machine learning may include regression, instance-based methods, regularization methods, decision tree, Bayesian, kernel methods, association rule learning, artificial neural networks, deep learning, dimensionality reduction, ensemble methods, the like, or any combination thereof. Regression may include partial least squares regression, ordinary least squares regression, logistic regression, multivariate adaptive regression splines, locally estimated scatterplot smoothing, the like, or any combination thereof.

After one or more data cleaning processes, data may be transmitted toward one or more dynamic digital profiles. Data associated with a user, event, or both may be transmitted toward a dynamic digital profile of the patient (DDPP), dynamic digital profile of the event (DDPE), or both. Data associated with a user may be transmitted toward both a dynamic digital profile of the patient (DDPP) and dynamic digital profile of the event (DDPE). Data associated with a specific event related to a user may be transmitted just to a dynamic digital profile of the event (DDPE). A specific event may be considered a user entry into the application which results in a diagnosis of one or more medical conditions.

A diagnosis method may include a step of determining a severity index. A severity index may function to determine a severity of one or more possible conditions. A severity index may function to determine a severity of data entered into one or more dynamic digital profiles (e.g., DDPE, DDPP). A severity index may function to assign a severity rating to a record entry within one or more dynamic digital profiles. For example, a patient severity index may be assigned to a record entered into a dynamic digital profile of the patient (DDPP). For example, an emergency severity index may be assigned to a record entered into a dynamic digital profile of the event (DDPE). Determining a severity index may be executed by one or more processors. The one or more processors may be of one of more user computing devices, diagnostic computing devices, the like, or a combination thereof. The determination may be automatically executed upon one or more data inputs being input, a user record being completed, a data conversion method being completed, or a combination thereof.

One or more machine learning methods may be used to determine one or more severity indexes. One or more types of machine learning may include regression, instance-based methods, regularization methods, decision tree, Bayesian, kernel methods, association rule learning, artificial neural networks, deep learning, dimensionality reduction, ensemble methods, the like, or any combination thereof. One or more artificial neural networks may include one or more multi-layer neural networks, one or more multi-classification neural networks, or both. A neural network may function my linking a plurality of nodes. The plurality of nodes may be within one or more input layers, hidden layers, output layers, or a combination thereof. The one or more input layers may be associated with one or more data inputs. For example, a patient neural network associated with the DDPE may be associated with one or more data inputs related to the event. As another example, an event neural network may be associated with the DDPP may be associated with one or more data inputs related to a patient. The one or more output layers may be one or more severity indexes. For example, an output layer of a DDPE may be the emergency severity index value. For example, an output layer of a DDPP may be the patient severity index value.

One or more severity indexes may be referred to as severity index values. One or more severity indexes may be representing by a ranking value. A ranking value may provide a ranking of the severity index from most severe to not severe. A ranking value may be based on a ranking scale. For example, a ranking scale of 1 to 5, 1 to 10, or even 1 to 100 may be used. The most severe ranking may be on either end of the ranking scale. For example, the lower end of the scale (e.g., 1) may be the most severe while the higher end of the scale (e.g., 5, 10, or 100) may be the least severe or vice-versa. For example, values 1, 2, and 3 may be designated as severe while values 4 and 5 may be designated as not severe. Each node may be responsible for a computation (e.g., execution of an algorithm). Each node may convert a user input to a numerical value. Each node may assign a weight to a user input. A severe severity index (e.g., 1, 2, or 3) may result in an immediate prompt for a user to seek emergency services (e.g., emergency condition menu, emergency prompt after critical symptom input); a later prompt to seek urgent care via emergency services and/or urgent care (e.g., diagnosis menu, medical care recommendation). A not severe severity index (e.g., 4 or 5) may result in a prompt for a user to seek medical care with their practitioner within a reasonable time.

A diagnosis method may include predicting a presence of one or more medical conditions. Predicting a presence of one or more medical conditions may allow for a user to identify if they are suffering a medical condition, what medical condition they may be experiencing, what medical care should be sought if any, or any combination thereof. Predicting a presence of one or more medical conditions may occur using one or more prediction processes. One or more prediction processes may include one or more condition tests, probability level comparisons, model executions, the like, or a combination thereof. Predicting may be executed by one or more processors. The one or more processors may be of one of more user computing devices, diagnostic computing devices, the like, or a combination thereof. The predicting may be automatically executed upon one or more data inputs being input, a user record being completed, a data conversion method being completed, a severity index being calculated, or a combination thereof.

One or more prediction processes may include performing one or more condition tests. One or more condition tests may function to determine which known conditions to compare to one or more user inputs, stored data, severity indexes, or any combination thereof. One or more databases may include one or more known conditions, data trends associated with the one or more known conditions (e.g., a "fingerprint"), or both. For example, a database may store a fingerprint of COVID-19, influenza, a common cold, and allergies. The fingerprint may be one or more symptoms associated with the one or more known conditions. Under one or more condition tests, stored data and/or severity indexes associated with a DDPP, DDPE, or both may be analyzed and compared to one or more known conditions and/or the fingerprint of one or more known conditions. During one or more condition tests, the stored data and/or severity indexes may be used for filtering one or more known conditions for those with common data patterns. One or more condition tests may be executed by filtering the database of known conditions, sorting the database of known conditions, or both for symptoms matching the user inputs, duration (e.g., number of days) of user inputs, severity of user inputs, medical history, and/or the like. One or more condition tests may be executed by machine learning.

One or more condition tests may be executed using one or more machine learning methods. One or more types of machine learning may include regression, instance-based methods, regularization methods, decision tree, Bayesian, kernel methods, association rule learning, artificial neural networks, deep learning, dimensionality reduction, ensemble methods, the like, or any combination thereof. Regression may include partial least squares regression, ordinary least squares regression, logistic regression, multivariate adaptive regression splines, locally estimated scatterplot smoothing, the like, or any combination thereof. One or more condition tests may result in one or more probabilities associated with a plurality of known conditions. For example, each known condition may be associated with a probability. The probability may be a probability of a user experiencing the known condition. Probability may be based on the symptoms, duration of symptoms, severity of symptoms, the user medical history, and/or the like.

One or more prediction processes may include performing one or more probability level comparisons. One or more probability level comparisons may include filtering one or more probabilities associated with one or more known conditions, one or more probabilities resulting from one or more condition tests, or both. One or more probability level comparisons may include filtering one or more probabilities to determine which known conditions to process through model execution, which one or more conditions are fairly probable, what the diagnosis may be, or any combination thereof. One or more probability level comparisons may include comparing one or more resulting probabilities of known conditions to one or more threshold probability levels. If the probability for a known condition is greater than or equal to a threshold probability level, the probability level comparison may be indicative a user may be suffering of that known condition. If the probability level for a known condition is less than a threshold probability level, the probability level comparison may be indicative the user may or may not be suffering of that known condition. The threshold probability level may be obtained from a threshold index table. If the probability level comparison is indicative that a user may be suffering of a known condition, the prediction process may be completed, may move on to the diagnosis, or both. If the probability level comparison is not certain if the user is suffering of a known condition, the prediction process may be stopped, move on to a model selection, or both.

The probability level comparison may refer to a threshold index table. A threshold index table may include a variety of predetermined threshold probability levels associated with a plurality of known conditions. The predetermined threshold probability levels may be predefined based on the known condition, one or more severity index values, or both. The predetermined threshold probability levels may be calculated by one or more machine learning models. The predetermined threshold probability levels may be based on data stored within a system database. One or more machine learning models may analyze data associated with a plurality of conditions stored within the database to determine the predetermined threshold probability levels. For example, a threshold index table may provide a threshold probability value based on a combination of the known condition, an emergency severity index value and a patient severity index value.

The prediction process may include executing one or more model selection processes. Executing one or more model selection processes may allow for better certainty to be determined if an initial probability level comparison did not indicate a user may be suffering a known condition. One or more probability level comparisons may include one or more machine learning methods. One or more probability level comparisons may include a plurality of machine learning methods used in combination. One or more types of machine learning may include regression, instance-based methods, regularization methods, decision tree, Bayesian, kernel methods, association rule learning, artificial neural networks, deep learning, dimensionality reduction, ensemble methods, the like, or any combination thereof. Regression may include partial least squares regression, ordinary least squares regression, logistic regression, multivariate adaptive regression splines, locally estimated scatterplot smoothing, the like, or any combination thereof. One or more model selection processes may include using a model different than a default model for that condition, a same model as the default model with a different design, model combinations in a certain sequence, the like, or any combination thereof. For example, a model selection process use include use of a logistic regression model combined with other models like Naïve Bayes and/or Random Forest Models combined in a predetermined sequence associated with a certain condition. One or more models (e.g., machine learning models) may be selected from a model toolbox. A model toolbox may be a repository of validated models. The validated models may include one or more machine learning models, mathematical models, empirical models, the like, or a combination thereof. As additional data (e.g., user inputs) are added into the system, the model toolbox may be continuously updated. Validated models may be frequently tested models which yield the best certainties of the presence of one or more conditions. The certainties may be determined based on known and/or verified medical conditions, patient severity index, emergency severity index, one or more user inputs, or any combination thereof. The one or more validated models may include a single, combination, sequence, or a combination thereof of one or more machine learning models, empirical models, mathematical models, the like, or any combination thereof. Once one or more models are selected, one or more models may be executed (e.g., model execution). Model execution may result in one or more probabilities values. Model execution may be similar to the one or more condition tests, but further analyzed for probably. After model execution, an iterative step of probability level comparison is completed. In other words, after model execution, the probability level comparison is repeated.

The diagnosis method may include identifying and outputting the presence and/or absence of one or more medical conditions. This step may function to inform a user of a condition they may be experiencing, or the absence thereof the severity of the condition; recommend medical care; recommend one or more medical facilities; provide a status update; or any combination thereof. The identifying and outputting may take place on one or more diagnosis menus. The one or more diagnosis menus may display the one or more conditions and/or severity identified from the one or more prediction processes.

Vital Approximation Method

The teachings of the present application relate to a vital approximation method using the system according to the teachings herein. The vital approximation method may use one or more user inputs related to a user account to determine one or more vitals. The vital approximation method may be useful when a user does not have one or more sensing devices readily available, inputs a vital description, inputs a vital estimate, or any combination thereof. The vital approximation method may result in one or more vital values which can be used within the diagnosis method. The vital approximation method may comprise one or more of the following steps: receiving one or more data inputs from a user related to one or more vitals which are only descriptions or estimates; retrieving one or more trends associated with the one or more vitals of the user and/or general population; calculating a vital value approximation; determining an impact of the value on a diagnosis method; and providing and/or retaining the vital value approximation to the diagnosis method. The vital approximation method may be executed by one or more processors. The one or more processors may be of one of more user computing devices, diagnostic computing devices, the like, or a combination thereof. The predicting may be automatically executed upon one or more vital approximations being provided by a user, as part of a user record, or both.

The vital approximation method may include receiving one or more data inputs related to one or more vitals which are only descriptions or estimates. The vital approximation method may be useful in converting these descriptions and/or estimates into more reliable numerical values. The one or more data inputs may be received from an application, a user interface, a user computing device, user, or a combination thereof. The one or more data inputs may be input by a user as numerical values, text, voice, images, the like, or a combination thereof. If unstructured, the one or more data inputs may be converted to structured data using one or more machine learning methods, data extraction processes, or both.

The vital approximation method may include retrieving one or more trends associated with the one or more vitals from the user, a general population, or both. The one or more trends may be used to assist in comparing to and/or converting the one or more vital descriptions and/or estimates to one or more vital values. The one or more trends may be retrieved from one or more databases. The one or more trends may be retrieved from a dynamic digital profile of the patient (DDPP) associated with the user.

The vital approximation method may include calculating one or more vital values. The one or more vital values may be useful within the diagnosis method, provide better accuracy than a vital description or estimate, or any combination thereof. Calculating one or more vital values may include using the one or more vital value approximations to filter for one or more similar or identical known vital values in a stored repository, associating the approximation with the known vital value, or both. Calculating one or more vital values may include one or more types of machine learning. One or more types of machine learning may include regression, instance-based methods, regularization methods, decision tree, Bayesian, kernel methods, association rule learning, artificial neural networks, deep learning, dimensionality reduction, ensemble methods, the like, or any combination thereof. Regression may include partial least squares regression, ordinary least squares regression, logistic regression, multivariate adaptive regression splines, locally estimated scatterplot smoothing, the like, or any combination thereof. For example, calculating one or more vital values may include multivariate, line regression.

The vital approximation method may include providing and/or retaining the vital value approximation to the diagnosis method. The vital approximation method may be useful in determining if the vital value approximation may or may not negatively impact a diagnosis generated by a diagnosis method. The vital approximation method may include performing a probability level comparison. One or more probability level comparisons may include comparing one or more vital value approximations to one or more threshold probability levels. If the probability of a vital value approximation is greater than or equal to a threshold probability level, the probability level comparison may be indicative that the vital value approximation may be good for using in the diagnosis method, prediction process, or both; may not negatively impact one or more results of the diagnosis method, prediction process, or both; or a combination thereof. If the probability of a vital value approximation is greater than or equal to a threshold probability level, than the vital value approximation is provided to the diagnosis method. If the probability of a vital value approximation method is less than a threshold probability level, the probability level comparison may be indicative that the vital value approximation may negatively impact the accuracy of the diagnosis method. If the probability of a vital value is less than a threshold probability level, than the vital value approximation may be withheld and/or retained from diagnosis method, prediction process, or both. The probability level comparison may refer to a vital threshold index table. A vital threshold index table may include a variety of predetermined vital threshold probability levels associated with a plurality of vital values, estimates, descriptions, or a combination thereof. The vital threshold probability levels may be predefined based on the known condition, known vital vales, one or more severity index values, or a combination thereof.

Training Method

The diagnosis method, vital approximation method, or both may include one or more methods of machine training. Training allows for one or more machine learning methods to identify one or more user data inputs, stored data, severity index values, or any combination thereof indicative of one or more conditions. Training may be particularly beneficial for the system of the present teachings. Training may include supervised learning, unsupervised learning, reinforcement learning, the like, or any combination thereof. The more data that is collected and analyzed, the more accurate the detection of one or more conditions may be. The training method may be completed in a live mode, offline mode, or both. The offline mode may analyze and learn from trends of previously recorded data. For example, one or more public health databases may already include data for a plurality of individuals. The data may include current symptoms, vitals, a diagnosed condition, and a severity. Using these previously recorded data, the machine learning is able to identify one or more trends (e.g., "fingerprints") of user data associated with one or more conditions and their severity. The live mode may collect data from one or more subjects (e.g., humans) and simultaneously capture their health data. The health data may be input by the user via a user interface as one or more data inputs. The user may input a known condition on the interface. The user may also log back into the system and update their medical condition and severity. Training may be executed by one or more processors. The one or more processors may be of one of more user computing devices, diagnostic computing devices, the like, or a combination thereof.

CASE EXAMPLES

Example A: Aneurysm

A user may log in into the application via the log-in menu. The user may be prompted to a vitals menu. The user may input their vitals which may not significantly deviate from their usual vitals. The user may input one or more critical symptoms in the emergency condition menu. One or more critical symptoms may include a sudden and severe headache, vomiting, confusion, and blurred vision. These symptoms generate an emergency prompt before the user is prompted to a daily symptoms menu. These symptoms may generate an immediate diagnosis of a possible aneurysm.

Example B: Heart Attack

A user may log in into the application via the log-in menu. The user may be prompted to a vitals menu. The user may input their vitals which may not significantly deviate from their usual vitals. Or the user may input a vital associated with an increased heart rate. The user may input one or more critical symptoms in the emergency condition menu. One or more critical symptoms may include chest pain, dizziness, indigestion, and extreme sweating. These symptoms generate an emergency prompt before the user is prompted to a daily symptoms menu. These symptoms may generate an immediate diagnosis of a possible heart attack.

Example C: COVID-19

A user may log in into the application via the log-in menu. The user may be prompted to a vitals menu. The user may input one or more vitals which deviate from their usual vitals. The user may input a temperature of above 100° F. The user may not enter any critical symptoms. The user may be prompted to a daily symptoms menu. The user may input current symptoms of cough, fever, sore throat, and muscle aches. These symptoms may generate a diagnosis of COVID-19 with a low severity.

A user may log in into the application via the log-in menu. The user may be prompted to a vitals menu. The user may input one or more vitals which deviate from their usual vitals. The user may input a temperature of above 100° F. The user may not enter any critical symptoms. The user may be prompted to a daily symptoms menu. The user may input current symptoms of difficulty breathing, cough, fever, sore throat, diarrhea, and muscle aches. These symptoms may generate a diagnosis of COVID-19 with a high severity.

Illustrative Examples

Figure 2:
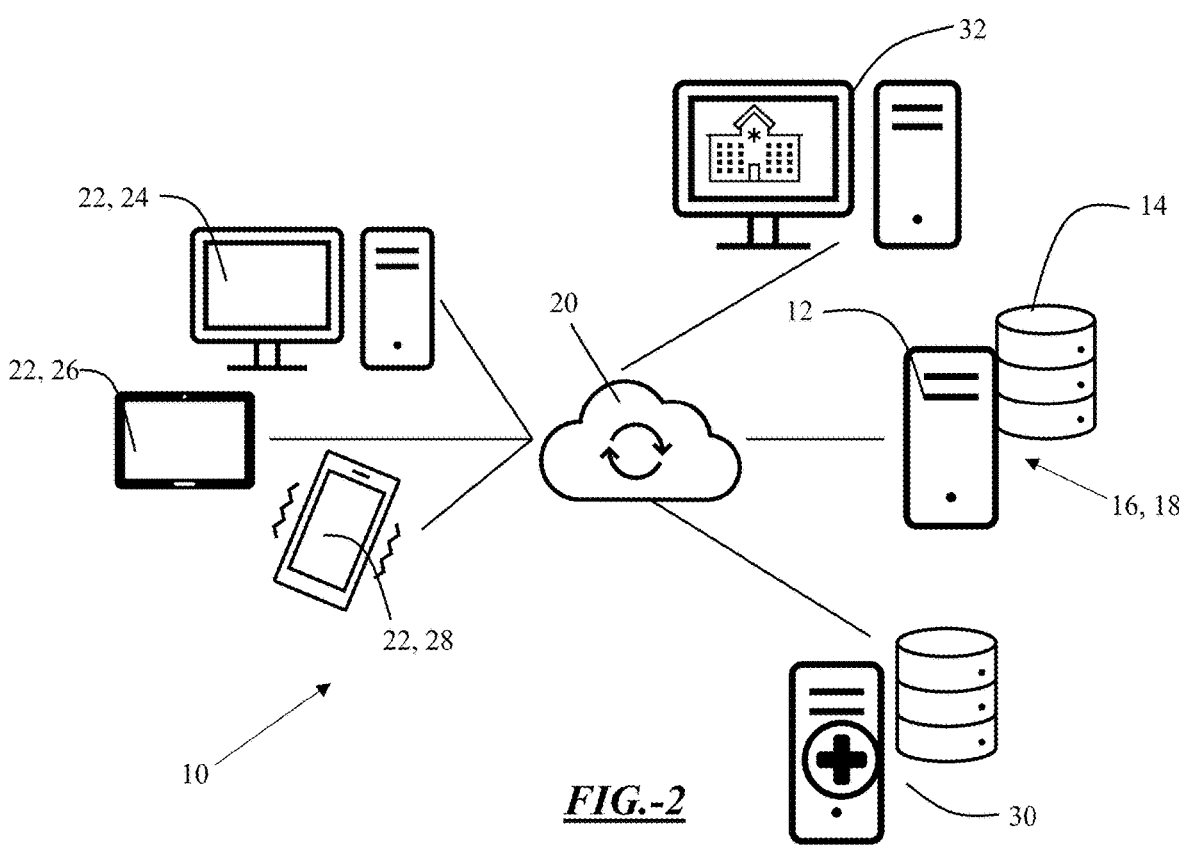
FIG. 2 illustrates a network diagram of a system according to the teachings herein.

FIGS. 1 and 2 illustrate network diagrams of a system 10. The system 10 includes a processor 12 and database 14. The processor 12 and database 14 may be together within a same server 16 or be separate and in communication with one another. The processor 12 and database 14 together may form a diagnostic computing device 18. The diagnostic computing device 18 is in communication with a network 20. The network 20 is in communication with a plurality of user computing devices 22. The user computing devices 22 can include computers 24, tablets 26, and mobile phones 28. The network 20 may also be in communication with one or more patient record systems 30 and/or medical facility systems 32.

Figure 3:
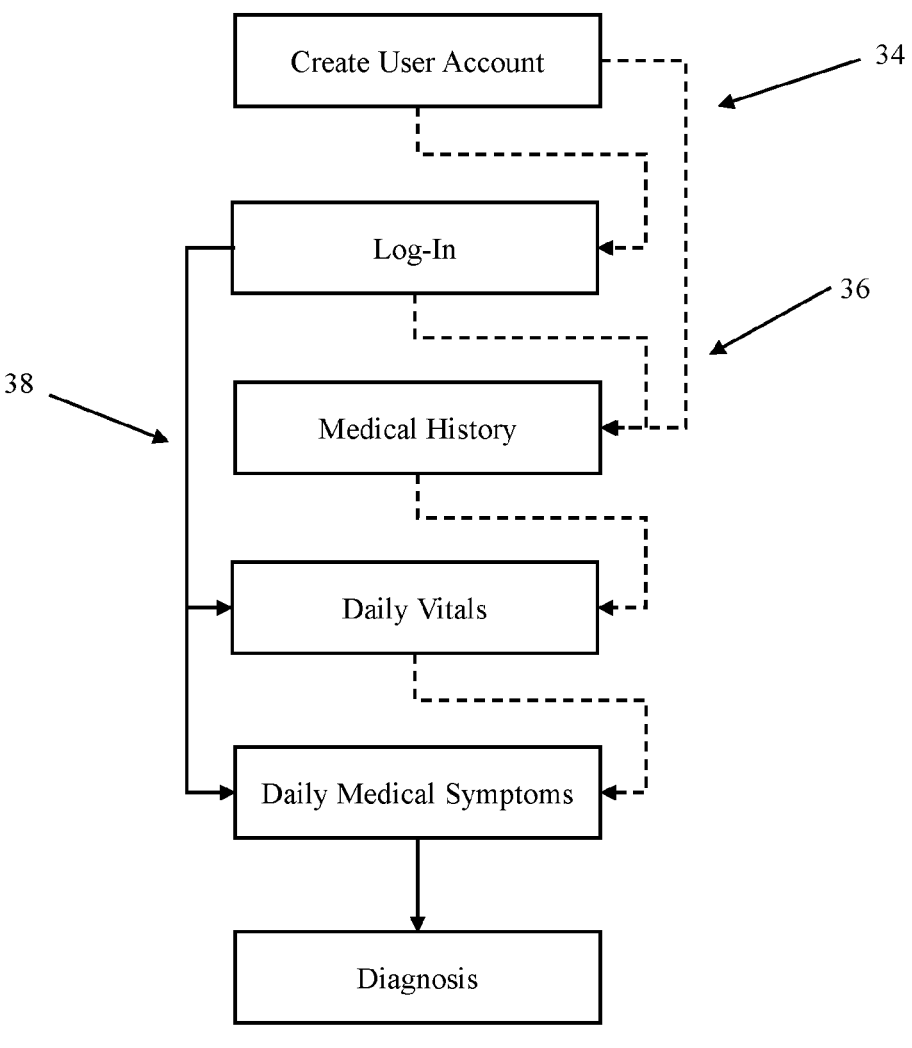
FIG. 3 illustrates a process flow of a user interacting with a system according to the teachings herein.

FIG. 3 illustrates a diagnosis process 34 of a user interacting with the system 10 (not shown) via a user computing device 22 (not shown). The user may be guided through an initial account creation process 36 (as shown by dotted lines) or through a regular diagnosis process 38 (as shown by solid lines). An account creation process 36 begins with a user creating their account. After creating their account, they may be prompted to log in or directed to inputting their medical history. After medical history, the user may be prompted to providing their daily (e.g., current vitals). After their vitals, the user may be prompted to providing their daily medical symptoms. After receiving the user's information, the system may then generate a diagnosis. A regular diagnosis process may begin at a user logging in to their account, providing their daily vitals, providing their daily medical symptoms, and then receiving their diagnosis. The steps in the diagnosis process 34 may be followed in other sequences. For example, daily medical symptoms may be inputted before daily vitals.

FIGS. 4A-4G illustrate a user interface 40 of a user computing device 22.

Figures 4A, 4B:
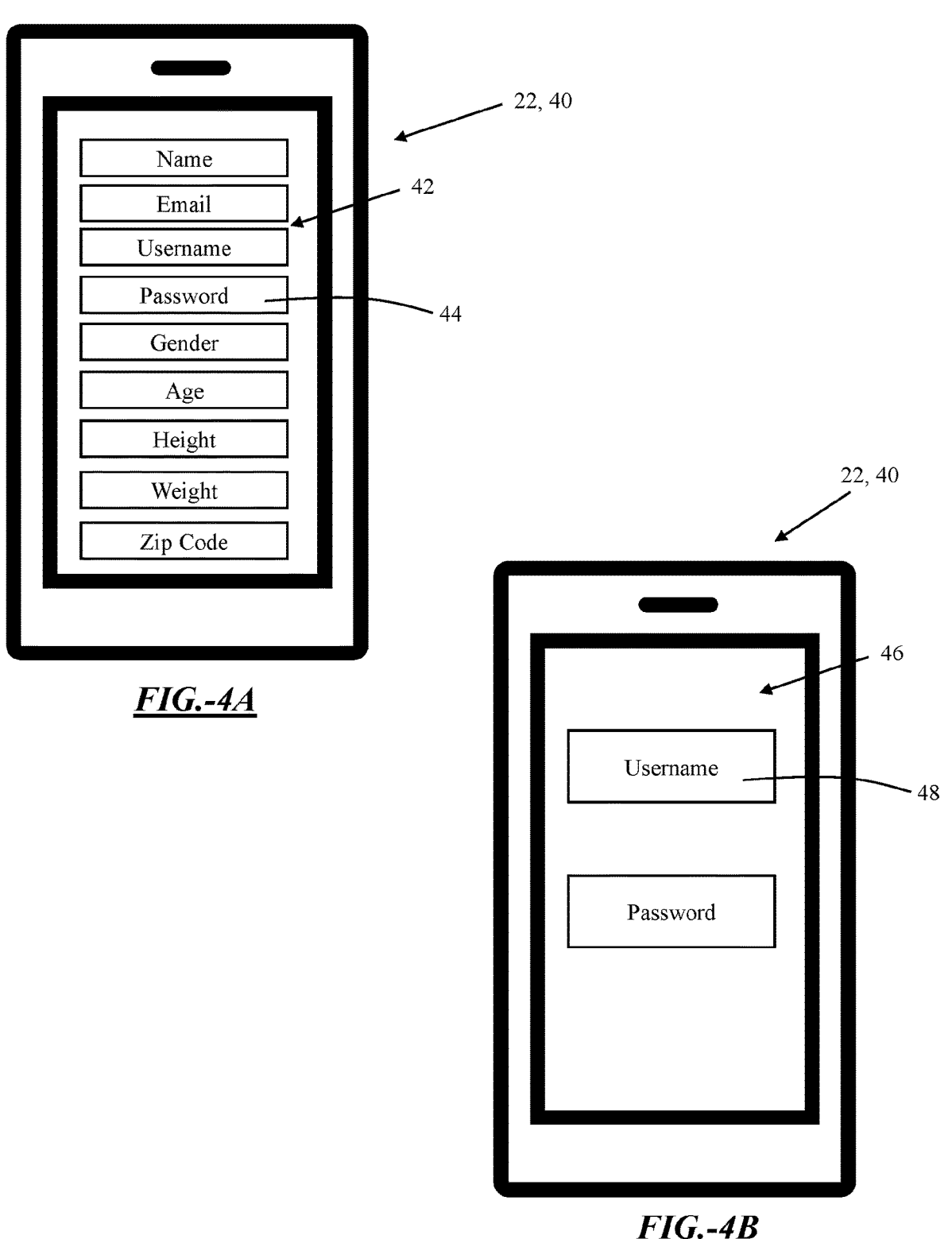
FIG. 4A illustrates a user interface of the system according to the teachings herein.
FIG. 4B illustrates a user interface of the system according to the teachings herein.

FIG. 4A shows an account creation menu 42. At the account creation menu 42 a user is prompted to enter in identification data 44. The identification data 44 can include a user's name, email, username, account password, gender, age, height, weight, zip code, the like, or a combination thereof. The identification data 44 may be displayed on a single screen or in a sequence of two or more screens.

FIG. 4B illustrates a log-in menu 46. The user is prompted to enter their account log-in information 48, such as their username and password.

Figures 4C, 4D:
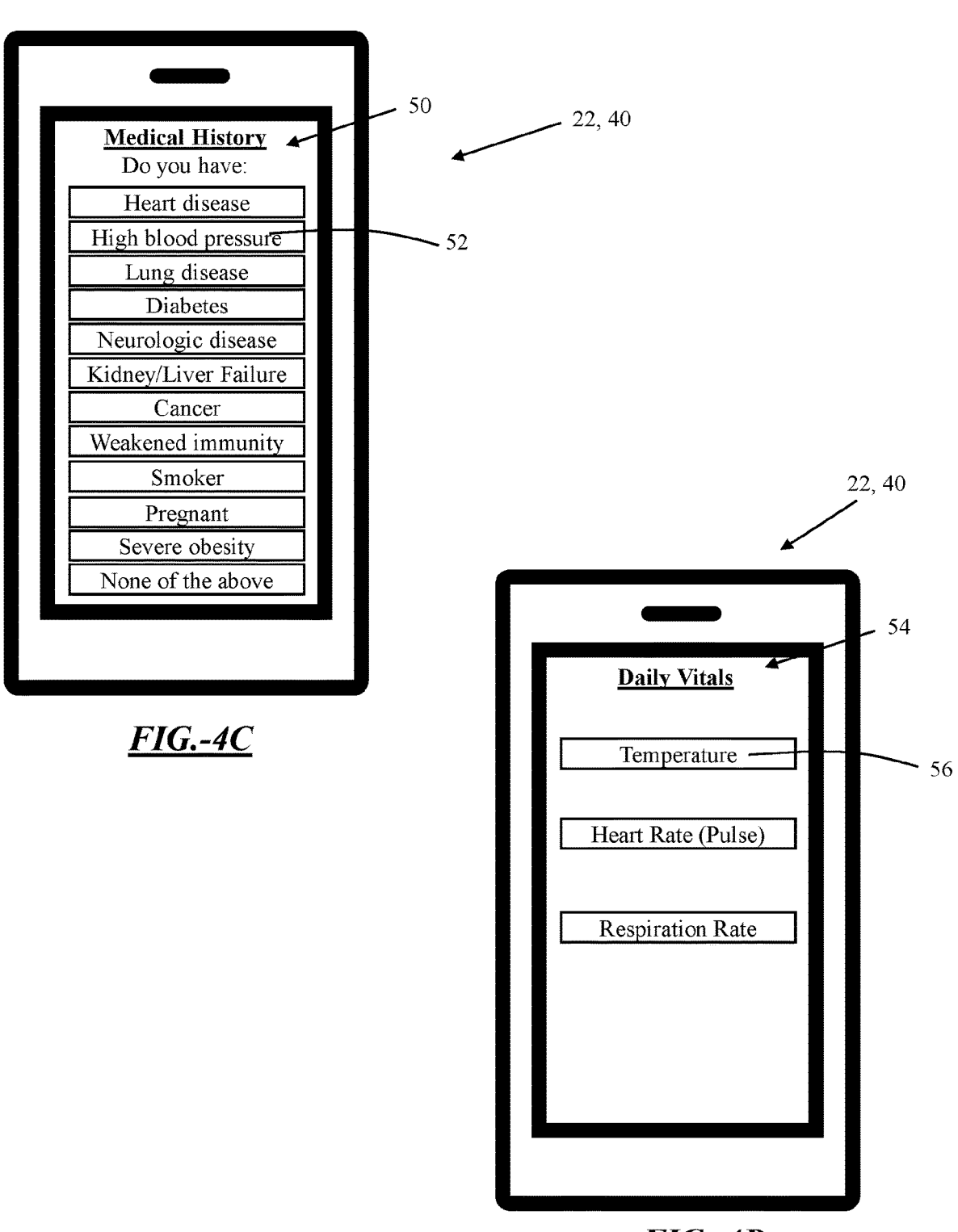
FIG. 4C illustrates a user interface of the system according to the teachings herein.
FIG. 4D illustrates a user interface of the system according to the teachings herein.

FIG. 4C illustrates a medical history menu 50. The user is prompted to enter any medical conditions 52 they currently have or have had. There may be one or more medical history submenus (not shown). For example, if a user selects "cancer" a submenu may appear asking for a specific type of cancer (e.g., lung, skin, etc.).

FIG. 4D illustrates a vitals menu 54. The vitals menu 54 prompts a user to enter in their vitals 56. The vitals 56 may be shown on a single screen or the user may be prompted through a plurality of screens. For example, each vital may be input in its own screen.

Figures 4E, 4F:
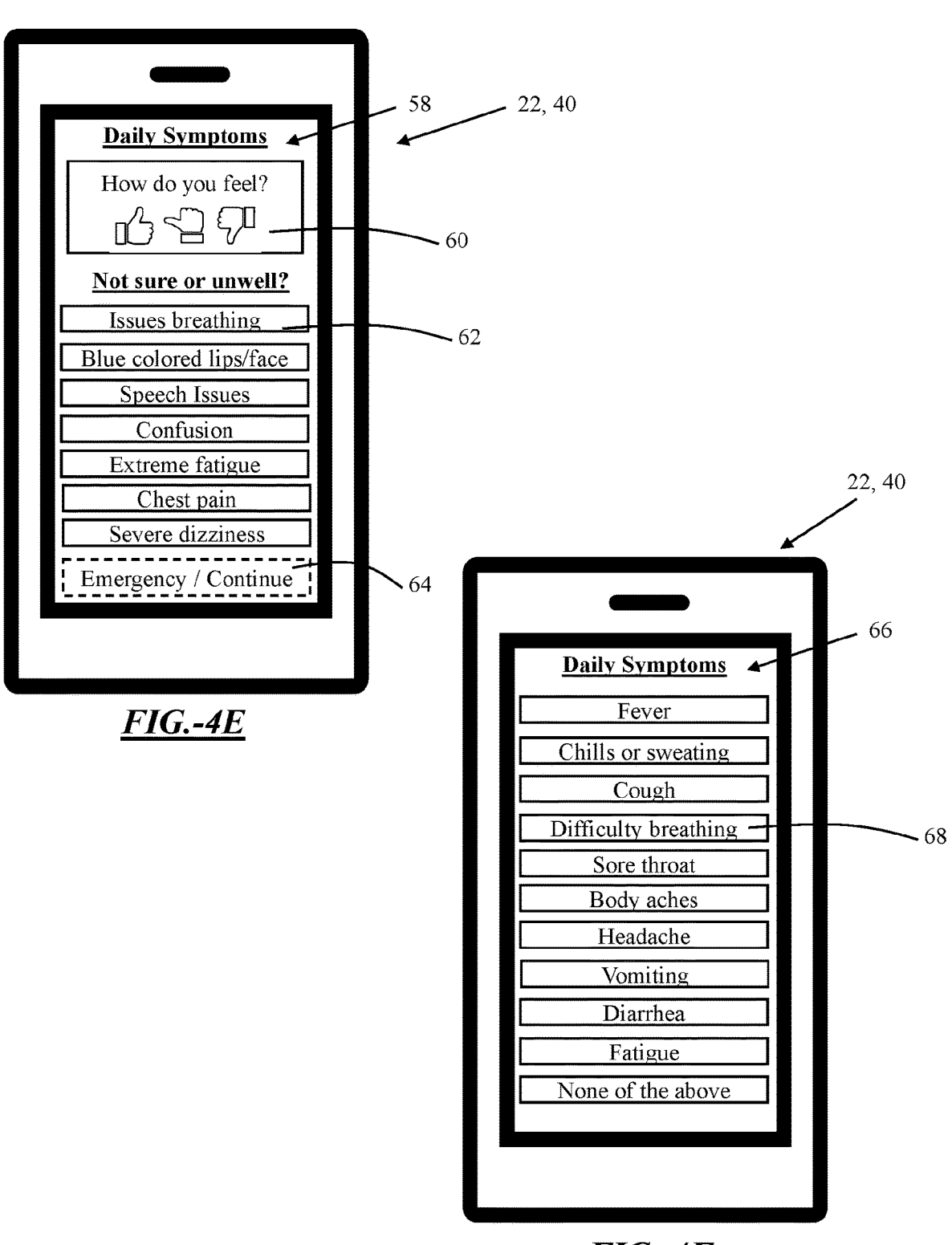
FIG. 4E illustrates a user interface of the system according to the teachings herein.
FIG. 4F illustrates a user interface of the system according to the teachings herein.

FIG. 4E illustrates an emergency condition menu 58. The user is prompted to enter in an overall wellbeing status 60. The user is also prompted to submit any critical medical symptoms 62. If any critical medical symptoms 62 are selected, an emergency prompt 64 may be displayed.

FIG. 4F illustrates a daily symptom menu 66. The user is prompted to enter in any current symptoms 68 they may be experiencing.

Figure 4G:
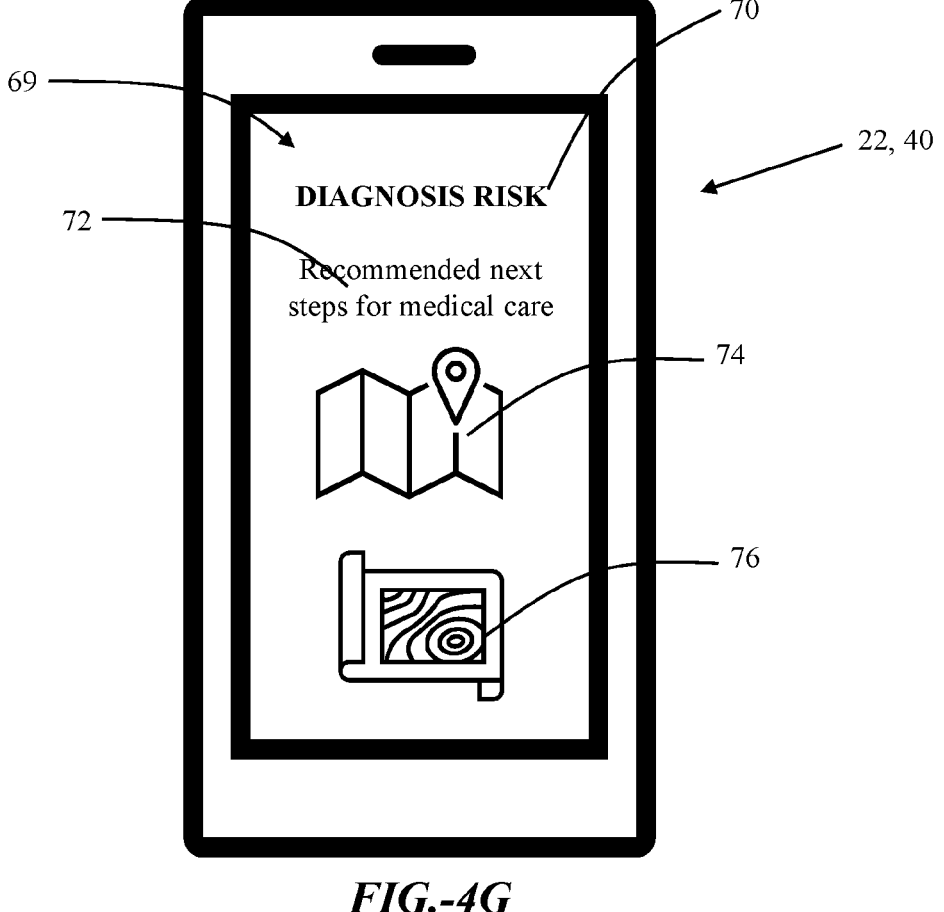
FIG. 4G illustrates a user interface of the system according to the teachings herein.

FIG. 4G illustrates a diagnosis menu 69. The diagnosis menu 69 displays a diagnosis risk 70 and a medical care recommendation 72. The diagnosis menu 69 may display nearby medical care facilities 74. The diagnosis menu 68 may display a general status update 76.

FIG. 5 illustrates a method 100 for using the system 10 (not shown) to determine a diagnosis risk 70 (not shown) and medical care recommendation 72 (not shown). The method may be a diagnosis process 34. The method 100 considers both a dynamic digital profile of a patient (DDPP) 78 and a dynamic digital profile of the event (DDPE) 80. The DDPP 78 utilizes information from overall health history and trends of the patient from data sources 82 and data types 84. The DDPE 80 utilizes event information of the patient from event data sources 86 and event features 88. The method uses the data from both the DDPE 80 and the DDPP 78 for a rating algorithm 90. After determining a rating algorithm 90, the method moves on to a prediction process 96. After the prediction process 96, the method outputs a diagnosis risk 70 and/or medical care recommendation 72. If some vitals 56 are unknown, the method can approximate those vitals. After, or even before, a rating algorithm 90 a vital approximation algorithm 92 may be executed. After the approximation algorithm 92 there may be an updated rating algorithm 90 executed.

Figure 6:
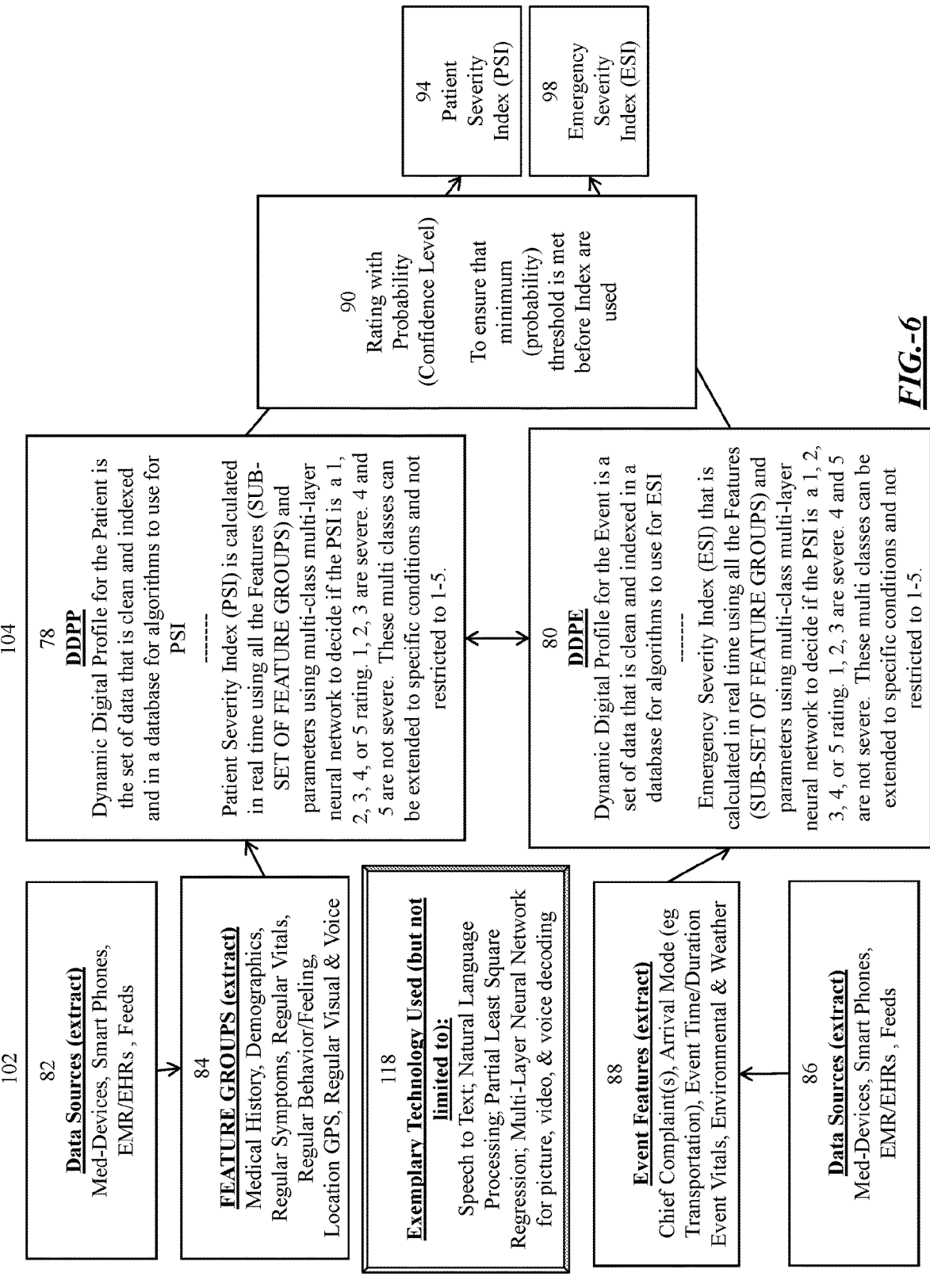
FIG. 6 illustrates a method for determining a severity index according to the teachings herein.

FIG. 6 illustrates a method for determining a patient severity index (PSI) 94 and an emergency severity index (ESI) 98. A patient severity index 94 relies on data sources 82 and data types 84. The data collected from data sources 82 and data types 84 is collected within a dynamic digital profile of the patient 78. Using a rating algorithm 90 a patient severity index 94 is determined. An emergency severity index 98 relies on event features 88 and event data sources 86. The data collected from the event features 88 and event data sources 86 is collected within a dynamic digital profile of the event 80. Using a rating algorithm 90 an emergency severity index is determined. Data sources 82, data types 84, event data sources 86, and event features 88 are considered data inputs 102. One or more data inputs 102 may be converted by one or more data cleaning techniques 118 before being saved as stored data 104. The stored data 104 may be the data saved within a dynamic digital profile for the patient 78 and/or the dynamic digital profile for the event 80.

Figure 7:
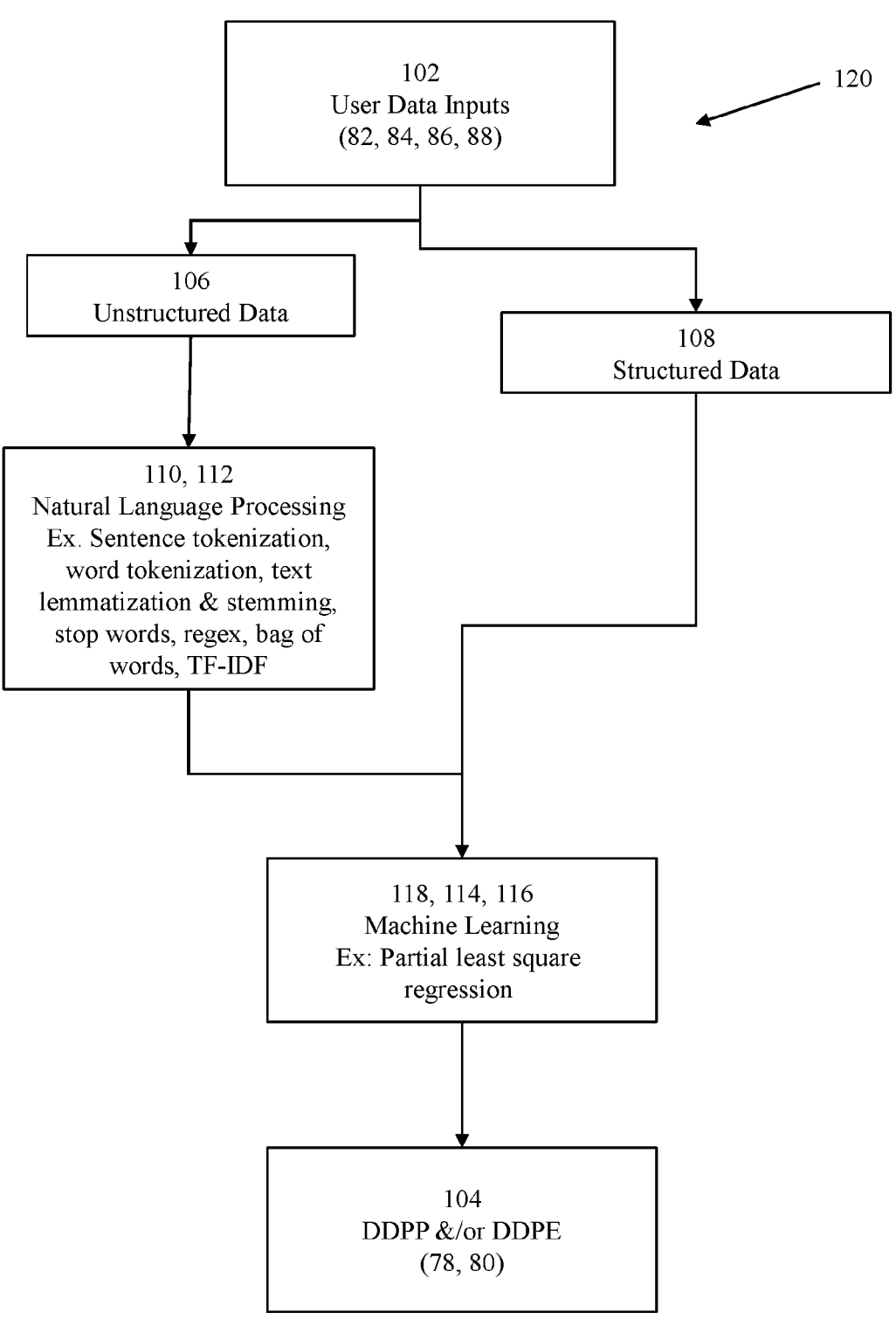
FIG. 7 illustrates a data conversion method according to the teachings herein.

FIG. 7 illustrates a data conversion method 120. The data conversion method 120 may be used for converting user data inputs 102 to stored data 104. The user data inputs 102 may be received unstructured data 106 or structured data 108. Unstructured data may go through a data extraction process 110. The data extraction process 110 may include natural language processing 112 or other data extraction steps. The data may be processed by one or more data cleaning techniques 118. The data cleaning techniques 118 may include one or more machine learning techniques 114, such as partial least square regression 116. The data may then be considered "clean data" and stored as stored data 104 within databases associated with the dynamic digital profile of the patient (DDPP) 78 and/or dynamic digital profile of the event (DDPE) 80.

Figure 8:
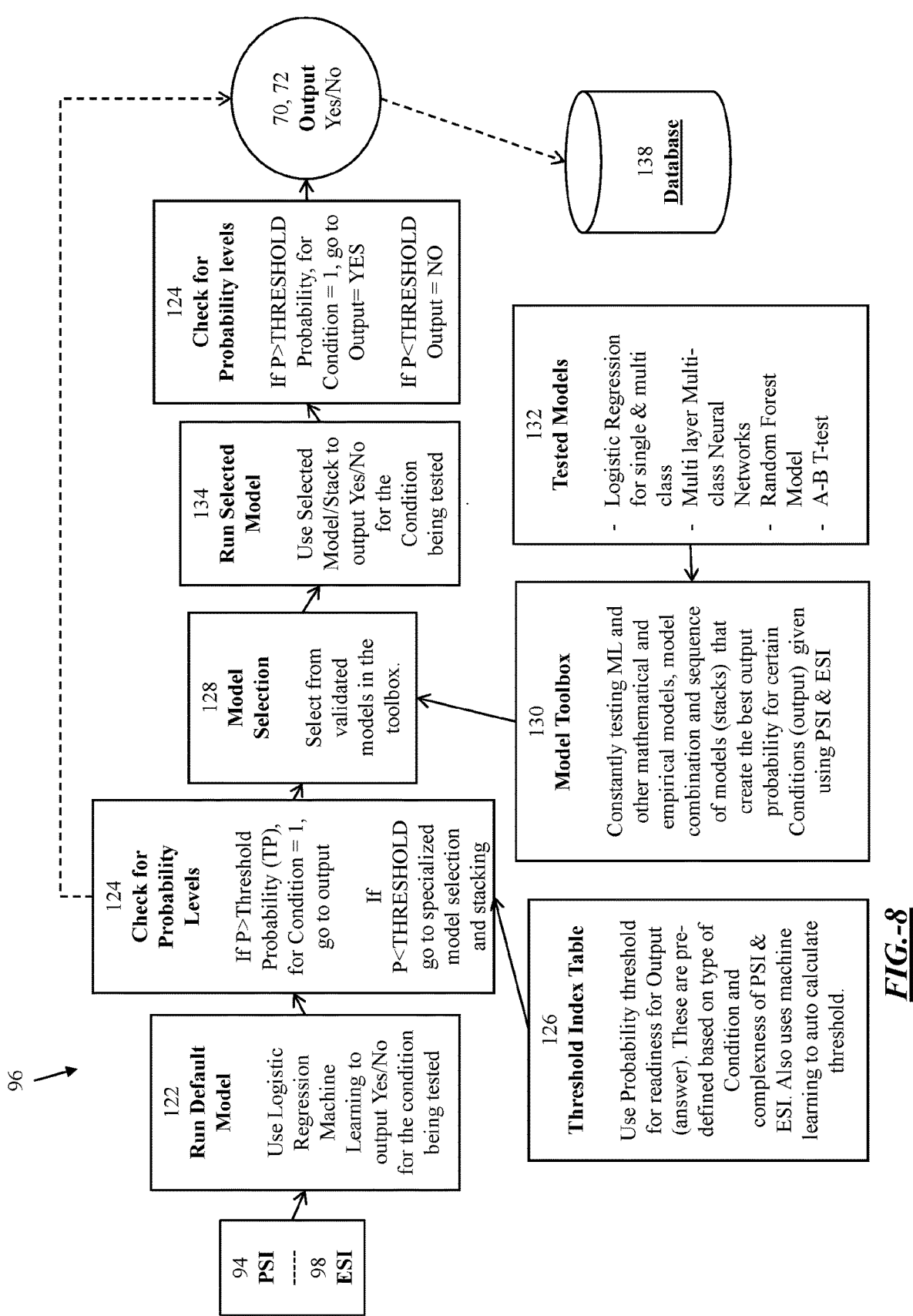
FIG. 8 illustrates a prediction process according to the teachings herein.

FIG. 8 illustrates the prediction process 96. The prediction process 96 begins by utilizing the patient severity index 94 and the emergency severity index 98. These indexes 94, 96 are inputted into a default model 122. The default model 122 may use logistic regression machine learning. The default model 122 may generate a probability level P. After the default model 122, there is a probability level comparison 124. The probability level P is compared to a threshold probability TH. The threshold probability TH is found using a threshold index table 126. If the probability P is greater than or equal to the threshold probability TH, then the prediction process 96 moves on to outputting a diagnosis risk 70 and/or medical care recommendation 72. If the probability P is less than the threshold probability TH, the prediction process moves to a model selection 128. The model selection 128 utilizes validated model from a model toolbox 130. The model toolbox 130 uses validated models for tested models 132. Using the validated model, model execution 134 is performed. Model execution 134 outputs an updated probability P. A probability level comparison 124 is executed using the updated probability. If the probability P is greater than or equal to the threshold probability TH, then the prediction process 96 moves on to outputting a diagnosis risk 70 and/or medical care recommendation 72. If the probability P is less than the threshold probability TH, then no diagnosis risk 70 and/or medical care recommendation 72 is provided.

FIG. 9 illustrates data collection and output of a database 138. The database 138 may be part of the system 10 (not shown). The database 138 receives the results of the diagnosis risk 70 and/or medical care recommendations 72. For example, simultaneously or after the diagnosis risk 70 and medical care recommendation 72 are outputted to a user interface 40, associated data may be transmitted to the database 138. The database 138 also receives data feeds 140, 142. The data feeds can be from public datasets, corporate and/or private datasets, academic institution owned datasets, government and/or public body datasets, the like, or any combination thereof. The database 138 also both receives and transmits data associated with the dynamic digital profile of the patient (DDPP) 78 and the dynamic digital profile of the event (DDPE) 80. Data from the database 138 is able to be transmitted, filtered, sorted, and the like to provide for analytics 136 of the population and individual patients.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time and the like is, for example, from 1 to 90, preferably from 20 to 80, more preferably from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The terms "generally" or "substantially" to describe angular measurements may mean about +/−10° or less, about +/−5° or less, or even about +/−1° or less. The terms "generally" or "substantially" to describe angular measurements may mean about +/−0.01° or greater, about +/−0.1° or greater, or even about +/−0.5° or greater. The terms "generally" or "substantially" to describe linear measurements, percentages, or ratios may mean about +/−10% or less, about +/−5% or less, or even about +/−1% or less. The terms "generally" or "substantially" to describe linear measurements, percentages, or ratios may mean about +/−0.01% or greater, about +/−0.1% or greater, or even about +/−0.5% or greater.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. An automated diagnosis method executed by one or more computing devices comprising:

a) receiving a plurality of data inputs including (i) one or more data inputs inputted by a user into a user computing device, (ii) one or more data inputs from one or more sensing devices, and (iii) one or more data inputs from one or more other applications;

wherein the one or more sensing devices detect and measure one or more vital signals one or more physiological signals, or both;

wherein the one or more sensing devices are separate from the user computing device;

wherein the user computing device is a mobile computing device including a screen, a microphone, and a camera;

wherein the one or more data inputs inputted by the user include the user vocally describing one or mot oms being experienced by the user using the microphone of the user computing device;

wherein the one or more data inputs inputted by the user include the user uploading one or more images, one or more videos, or both showing at least one of the one or more symptoms experienced by the user using the camera of the user computing device; and wherein the one or more other applications include one or more fitness and health applications, one or more photograph applications, one or more navigation applications, or a combination thereof;

b) converting a plurality of data from the plurality of data inputs from the user the one of more sensing devices, and the one or more other applications into a stored data by one or more processors and storing within one or more storage mediums;

wherein the converting is automatically executed after receiving the plurality of inputs;

wherein at least some of the plurality of data is unstructured data and the converting includes converting the unstructured data to a structured data; and wherein the converting of the unstructured data to the structured data includes natural language processing; speech to text; and data cleaning to decode at least some of the one or more data inputs received as the one or more images and/or the one or more videos, and a voice;

c) determining one or more severity indexes based on the stored data with the one or more processors, wherein the determining of the one or more severity indexes includes converting the stored data in one or more dynamic digital profiles into the one or more severity indexes, and wherein the stored data in a dynamic digital profile of an event is used to determine an emergency severity index value based at least in part on an event time and an event duration;

wherein the determining of the one or more severity indexes is automatically executed upon the converting of the plurality of data being completed;

wherein the stored data and the one or more dyna mic digital profiles are stored within one or more databases;

wherein the one or more dynamic digital profiles include a dynamic digital profile of a patient and the dynamic digital profile of the event;

wherein the dynamic digital profile of the patient utilizes information from health history and trends, including medical history, demographics, regular symptoms, regular vitals, regular behavior, regular feeling, location GPS, regular visuals, and regular voice; and wherein the dynamic digital profile of the event utilizes event information including one or more chief complaints an arrival mode, the event time the event duration, event vitals, environment, and weather;

d) predicting a presence of one or more medical conditions based on the one or more severity indexes by the one or more processors;

wherein the predicting the presence of the one or more medical conditions is automatically executed upon the determining the one or more severity indexes;

wherein the predicting be presence of the one or more medical conditions includes performing one or more condition tests, which include comparing the stored data, the one or more severity indexes, or both to one or more known conditions and filtering for those with common data patterns;

wherein the one or more condition tests execute one or more machine learning models; and wherein the one or more machine learning models include one or more regression models;

e) identifying the presence of the one or more medical conditions to the user by transmitting an output containing the presence of the one or more medical conditions to the user computing device via the one or more processors onto a user interface of the user computing device; and wherein the output indicates a severity of the one or more medical conditions and provides one or more recommendations with respect to medical care and attention, including whether immediate medical attention is necessary.

2. The automated diagnosis method of claim 1, wherein the plurality of data inputs inputted by the user into the user computing device further include text, numbers, selection of buttons, or any combination thereof.

3. The automated diagnosis method of claim 1, wherein the user is logged into their account within an application being executed on the user computing device for the automated diagnosis method.

4. The automated diagnosis method of claim 1, wherein the one or more data inputs inputted by the user into the user computing device include one or more vitals, critical symptoms, current symptoms, or a combination thereof of the user.

5. The automated diagnosis method of claim 1, wherein the converting of the plurality of data includes executing one or more machine learning models.

6. The automated diagnosis method of claim 5, wherein the one or more machine learning models include one or more regression models.

7. The automated diagnosis method of claim 1, wherein the dynamic digital profile of the patient includes the stored data related to each occurrence when the user submits data into the user interface and one or more user inputs.

8. The automated diagnosis method of claim 1, wherein the dynamic digital profile of the patient includes the stored data which results in the one or more medical conditions being identified.

9. The automated diagnosis method of claim 1, wherein the determining of the one or more severity indexes uses one or more machine learning methods.

10. The automated diagnosis method of claim 9, wherein the one or more machine learning methods includes a multi-layer, multi-classification neural network.

11. The automated diagnosis method of claim 1, wherein the one or more known conditions with the common data patterns compared to the stored data and the one or more severity indexes are analyzed under one or more probability level comparisons; and wherein the one or more known conditions with a probability greater than or equal to a threshold probability value are determined as the one or more medical conditions.

12. The automated diagnosis method of claim 1, wherein the one or more medical conditions are displayed on a same user interface, including the screen, in which the plurality of data inputs are entered by the user on the user computing device.

13. The automated diagnosis method of claim 1, wherein the one or more databases include one or more records;

wherein the one or more records store one or more data entries associated with one or more users including identification data, log-in information, medical history, medical conditions, vitals, emergency conditions, well-being, critical symptoms, current symptoms, or a combination thereof;

wherein the one or more users are associated with a user identification key; and wherein the one or more records in the one or more databases are filtered by the user identification key to execute one or more algorithms, processes, rules, or a combination thereof.

14. The automated diagnosis method of claim 1, wherein the one or more sensing devices include one or more thermometers, heart rate monitors, pulse oximeter, be included with one or more wearable accessories, or a combination thereof.

15. An automated diagnosis method executed by one or more computing devices comprising:

a) receiving a plurality of data inputs (i) inputted by a user into a user interface of a user computing device, (ii) received from one or more sensing devices, and (iii) received from one or more other applications;

wherein the plurality of data inputs include one or more vitals, a presence or an absence of critical symptoms, and a presence or an absence of current symptoms;

wherein the one or more sensing devices detect and measure the one or more vital signals, one or more physiological signals, or both;

wherein the one or more sensing devices are separate from the user computing device;

wherein the user computing device is a mobile computing device with the user interface which includes a screen, a microphone and a camera;

wherein one or more data inputs inputted by the user include the user vocally describing one or more symptoms being experienced by the user using the microphone of the user computing device;

wherein the one or more data inputs inputted by the user include the user uploading one or more images, one or more videos, or both showing at least one of the one or more symptoms using the camera of the user computing device; and wherein the one or more other applications include one or more fitness and health applications, one or more photograph applications, one or more navigation applications, or a combination thereof;

b) converting a plurality of data from the plurality of data inputs from the user, the one or more sensing devices, and the one or more other applications into a stored data by one or more processors and storing within one or more storage mediums, wherein the stored data is stored as part of a dynamic digital profile of a patient and a dynamic digital profile of an event;

wherein the converting is automatically executed after receiving the plurality of inputs;

wherein at least some of the plurality of data is unstructured data and the converting includes converting the unstructured data to a structured data;

wherein the converting the unstructured data to the structured data includes natural language processing: speech to text; and data cleaning to decode at least some of the one or more data inputs received as the one or more images and/or the one or more videos, and a voice;

wherein the dynamic digital profile of the patient and the dynamic digital profile of the event are stored within one or more databases;

c) determining one or more severity indexes based on the stored data with the one or more processors by converting the stored data in the dynamic digital profile of the patient and the dynamic digital profile of the event into the one or more severity indexes, and wherein the stored data in the dynamic digital profile of the event is used to determine an emergency severity index value based at least in part on an event time and an event duration;

wherein the determining of the one or more severity indexes is automatically executed upon the converting being completed;

wherein the dynamic digital profile of the patient utilizes information from health history and trends including medical history, demographics regular symptoms, regular vitals, regular behavior, regular feeling, location GPS, regular visuals, and regular voice;

wherein the dynamic digital profile of the patient includes the stored data related to each occurrence when the user submits the one or more data inputs into the user interface;

wherein the dynamic digital profile of the event utilizes event information including one or more chief complaints, arrival mode, the event time, the event duration, event vitals, environment, and weather;

wherein the dynamic digital profile of the event includes the stored data related to one or more occurrences when the user submits the one or more data inputs into the user interface which result in a diagnosis of the one or more medical conditions;

d) predicting a presence of one or more medical conditions based on the one or more severity indexes by the one or more processors;

wherein the predicting the presence of the one or more medical conditions is automatically executed upon the determining of the one or more severity indexes;

wherein the predicting the presence of the one or more medical conditions includes performing one or more condition tests, which include comparing the stored data, the one or more severity indexes, or both to one or more known conditions and filtering for those with common data patterns;

wherein the one or more condition tests execute one or more machine learning models; and wherein the one or more machine learning models include one or more regression models;

e) identifying the presence of the one or more medical conditions to the user, based on the predicting the presence of the one or more medical conditions, by transmitting an output containing the presence of the one or more medical conditions to the user interface of the user computing device via the one or more processors; and wherein the output indicates a severity of the one or more medical conditions and provides one or more recommendations with respect to medical care and attention, including whether immediate medical attention is necessary.

16. The automated diagnosis method of claim 15, wherein the predicting the presence of the one or more medical conditions includes the steps of:

i) automatically inputting a patient severity index and the emergency severity index into a default model to determine a probability level;

ii) automatically comparing the probability level to a threshold level obtained from a threshold index table;

ii-a) if the probability level is greater than or equal to the threshold level, the output of a diagnosis risk and/or medical recommendation is automatically provided;

ii-b) if the probability level is less than the threshold level, model selection is automatically performed from a model toolbox;

ii-b-i) model execution is automatically performed on a model selected during the model selection, and an updated probability is determined;

ii-b-ii) the updated probability is automatically compared to the threshold level;

ii-b-ii-a) if the updated probability is greater than or equal to the threshold level, the output of the diagnosis risk and/or medical recommendation is provided; and ii-b-ii-b) if the updated probability level is less than the threshold level, no diagnosis risk or medical recommendation is provided.

17. The automated diagnosis method of claim 16, wherein the model selection process further includes one or more probability level comparisons;

wherein the one or more probability level comparisons include filtering one or more probabilities associated with one or more known conditions, one or more probabilities resulting from one or more condition tests, or both; and wherein the one or more probability level comparisons include filtering one or more probabilities to determine which known conditions to process through model execution, which one or more conditions are fairly probable, what the diagnosis may be, or any combination thereof.

18. The automated diagnosis method of claim 15, wherein the one or more sensing devices include one or more thermometers, heart rate monitors, pulse oximeter, be included with one or more wearable accessories, or a combination thereof.

19. An automated diagnosis method executed by one or more computing devices comprising:

a) receiving a plurality of data inputs (i) inputted by a user into a user interface of a user computing device, (ii) received from one or more sensing devices, and (iii) received from one or more other applications; wherein the plurality of data inputs include one or more vitals, a presence or an absence of critical symptoms, and a presence or an absence of current symptoms;

wherein the one or more sensing devices detect and measure one or more vital signals, one or more physiological signals, or a combination thereof;

wherein the one or more sensing devices are separate from the user computing device;

wherein the user computing device is a mobile computing device with the user interface which includes a screen, a microphone, and a camera;

wherein one or more data inputs inputted by the user include a user vocally describing one or more symptoms experienced by the user using the microphone of the user computing device;

wherein one or more data inputs inputted by the user include the user uploading one or more images, one or more videos, or both showing at least one of the one or more symptoms using the camera of the user computing device; and wherein the one or more other applications include one or more fitness and health applications, photograph applications, navigation applications, or a combination thereof;

b) converting a plurality of data from the plurality of data inputs into a stored data by one or more processors and storing within one or more storage mediums, wherein the stored data is stored as part of a dynamic digital profile of a patient and a dynamic digital profile of an event;

wherein the converting is automatically executed after receiving the plurality of inputs;

wherein at least some of the plurality of data inputs are unstructured data and the converting includes converting the unstructured data to a structured data;

wherein the converting the unstructured data to the structured data includes natural language processing: speech to text; and data cleaning to decode one or more inputs received as the one or more images and/or the one or more videos, and a voice;

wherein the dynamic digital profile of the patient and the dynamic digital profile of the event are stored within one or more databases;

c) determining one or more severity indexes based on the stored data with the one or more processors by converting the stored data in the dynamic digital profile of the patient and the dynamic digital profile of the event into the one or more severity indexes, and wherein the stored data in the dynamic digital profile of the event is used to determine an emergency severity index value and the stored data in the dynamic digital profile of the patient is used to determine a patient severity index based at least in part on an event time and an event duration;

wherein the determining of the one or more severity indexes is automatically executed upon the converting of the plurality of data being completed;

wherein the dynamic digital profile of the patient utilizes information from health history and trends including medical history, demographics, regular symptoms, regular vitals, regular behavior, regular feeling, location GPS, regular visuals, and regular voice;

wherein the dynamic digital profile of the patient includes the stored data related to each occurrence when the user submits the one or more data inputs into the user interface;

wherein the dynamic digital profile of the event utilizes event information including one or more chief complaints, arrival mode, the event time, the event duration, event vitals, environment, and weather;

wherein the dynamic digital profile of the event includes the stored data related to one or more occurrences when the user submits the one or more data inputs into the user interface which result in a diagnosis of the one or more medical conditions;

d) predicting a presence of one or more medical conditions based on the one or more severity indexes by the one or more processors, wherein the predicting the presence of the one or more medical conditions includes the steps of:

i) automatically inputting the patient severity index and the emergency severity index into a default model to determine a probability level;

ii) automatically comparing the probability level to a threshold level obtained from a threshold index table;

ii-a) if the probability level is greater than or equal to the threshold level, an output of a diagnosis risk and/or medical recommendation is provided;

ii-b) if the probability level is less than the threshold level, model selection is automatically performed from a model toolbox;

ii-b-i) model execution is automatically performed on a model selected during the model selection, and an updated probability is determined;

iii-b-ii) the updated probability is automatically compared to the threshold level;

ii-b-iii-a) if the updated probability is greater than or equal to the threshold level, the output of a diagnosis risk and/or medical recommendation is provided; and ii-b-ii-b) if the updated probability level is less than the threshold level, no diagnosis risk or medical recommendation is provided;

wherein the predicting the presence of the one or more medical conditions is automatically executed upon the determining of the one or more severity indexes;

wherein the predicting the presence of the one or more medical conditions includes performing one or more condition tests which include comparing the stored data, the one or more severity indexes, or both to one or more known conditions and filtering for those with common data patterns;

wherein the one or more condition tests execute one or more machine learning models; and wherein the one or more machine learning models include one or more regression models;

e) identifying the presence of the one or more medical conditions to the user, based on the predicting the presence of the one or more medical conditions, by transmitting the output containing the presence of the one or more medical conditions to the user interface of the user computing device via the one or more processors; and wherein the output indicates a severity of the one or more medical conditions and provides one or more recommendations with respect to medical care and attention, including whether immediate medical attention is necessary.

20. The automated diagnosis method of claim 19, wherein the user is logged into their account within an application being executed on the user computing device for the automated diagnosis method.

\* \* \* \* \*